United States Patent
Follmann et al.

(10) Patent No.: US 9,498,480 B2
(45) Date of Patent: Nov. 22, 2016

(54) SUBSTITUTED AZABICYCLES AND USE THEREOF

(71) Applicant: Bayer Intellectual Property GmbH, Monheim (DE)

(72) Inventors: Markus Follmann, Köln (DE); Johannes-Peter Stasch, Solingen (DE); Gorden Redlich, Bochum (DE); Alexandros Vakalopoulos, Hilden (DE); Dieter Lang, Velbert (DE); Frank Wunder, Wuppertal (DE); Walter Hübsch, Wuppertal (DE); Michael Hahn, Langenfeld (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/382,746

(22) PCT Filed: Mar. 5, 2013

(86) PCT No.: PCT/EP2013/054427
§ 371 (c)(1),
(2) Date: Sep. 3, 2014

(87) PCT Pub. No.: WO2013/131923
PCT Pub. Date: Sep. 12, 2013

(65) Prior Publication Data
US 2015/0025090 A1    Jan. 22, 2015

(30) Foreign Application Priority Data
Mar. 6, 2012 (EP) .................................... 12158166

(51) Int. Cl.
| A61K 31/519 | (2006.01) |
| C07D 487/04 | (2006.01) |
| A61K 31/522 | (2006.01) |
| A61K 45/06 | (2006.01) |
| C07D 519/00 | (2006.01) |

(52) U.S. Cl.
CPC ........... *A61K 31/519* (2013.01); *A61K 31/522* (2013.01); *A61K 45/06* (2013.01); *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

| 4,833,246 | A | 5/1989 | Adachi et al. |
| 5,976,523 | A | 11/1999 | Awaya et al. |
| 6,166,027 | A | 12/2000 | Straub et al. |
| 6,180,656 | B1 | 1/2001 | Furstner et al. |
| 6,451,805 | B1 | 9/2002 | Straub et al. |
| 6,743,798 | B1 | 6/2004 | Straub et al. |
| 6,833,364 | B1 | 12/2004 | Straub et al. |
| 6,903,089 | B1 | 6/2005 | Stasch et al. |
| 7,173,037 | B2 | 2/2007 | Alonso-Alija et al. |
| 7,410,973 | B2 | 8/2008 | Feurer et al. |
| 7,414,136 | B2 | 8/2008 | Matsumura et al. |
| 7,541,367 | B2 | 6/2009 | Chiu et al. |
| 8,058,282 | B2 | 11/2011 | Adams et al. |
| 8,242,272 | B2 | 8/2012 | Jimenez et al. |
| 8,293,900 | B2 | 10/2012 | Jian et al. |
| 8,309,551 | B2 | 11/2012 | Schirok et al. |
| 8,420,656 | B2 | 4/2013 | Follmann et al. |
| 2004/0235863 | A1 | 11/2004 | Feurer et al. |
| 2008/0004257 | A1 | 1/2008 | Chan et al. |
| 2010/0298336 | A1 | 11/2010 | Attardo et al. |
| 2011/0218202 | A1 | 9/2011 | Brockunier et al. |
| 2012/0022084 | A1 | 1/2012 | Follmann et al. |
| 2012/0029002 | A1 | 2/2012 | Straub et al. |
| 2013/0072492 | A1 | 3/2013 | Raghavan et al. |
| 2013/0172372 | A1 | 7/2013 | Follmann et al. |
| 2013/0178475 | A1 | 7/2013 | Moore et al. |
| 2013/0210824 | A1 | 8/2013 | Follmann et al. |
| 2013/0338137 | A1 | 12/2013 | Follmann et al. |
| 2014/0100229 | A1 | 4/2014 | Follmann et al. |
| 2014/0148433 | A1 | 5/2014 | Follmann et al. |
| 2014/0171434 | A1 | 6/2014 | Follmann et al. |
| 2014/0228366 | A1 | 8/2014 | Follmann et al. |
| 2014/0249168 | A1 | 9/2014 | Follmann et al. |
| 2014/0350020 | A1 | 11/2014 | Follmann et al. |

(Continued)

FOREIGN PATENT DOCUMENTS

| CA | 2803688 A1 | 12/2011 |
| CA | 2804470 A1 | 1/2012 |

(Continued)

OTHER PUBLICATIONS

Byrn, Stephen. Solid-State Chemistry of Drugs, 2d, Chapter 11 Hydrates and Solvates/hydrates, 233-247, 233.*
Morissette, Sherry. Adv. Drug Delivery Rev. 2004, 56, 275-300.*
Nossaman, Vauhhn. Cardiol Rev. 18(4), (2010) 190-197.*
Mayo Clinic. Heart Failure. Prevention. (2015) Web. <http://www.mayoclinic.org/diseases-conditions/heart-failure/basics/prevention/con-20029801>.*
PubMed Health. Angina: Prevention. (2014) Web. <http://www.ncbi.nlm.nih.gov/pubmedhealth/PMH0062934/#nhlbisec-prevention>.*
NIH. Prevention of High Blood Pressure. (2015) Web. <http://www.nhlbi.nih.gov/health/health-topics/topics/hbp/prevention>.*
Healthgrades. What is Ischemia? (2013) Web. <http://www.healthgrades.com/conditions/ischemia>.*

(Continued)

*Primary Examiner* — Golam M Shameem
*Assistant Examiner* — Laura Daniel
(74) *Attorney, Agent, or Firm* — Buchanan Ingersoll & Rooney PC

(57) ABSTRACT

The present application relates to novel substituted azabicycles, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

6 Claims, No Drawings

(56) References Cited

U.S. PATENT DOCUMENTS

| | | | |
|---|---|---|---|
| 2014/0357637 | A1 | 12/2014 | Follmann et al. |
| 2015/0065533 | A1 | 3/2015 | Follmann et al. |
| 2015/0274754 | A1 | 10/2015 | Follmann |
| 2016/0002267 | A1 | 1/2016 | Follmann |

FOREIGN PATENT DOCUMENTS

| | | |
|---|---|---|
| CA | 2809911 A1 | 3/2012 |
| CA | 2834901 A1 | 11/2012 |
| CA | 2840886 A1 | 1/2013 |
| CN | 1613849 A | 5/2005 |
| EP | 0 634 413 A1 | 1/1995 |
| WO | 98/16223 A1 | 4/1998 |
| WO | 00/06569 A1 | 2/2000 |
| WO | 01/83490 A1 | 11/2001 |
| WO | 02/059083 A2 | 8/2002 |
| WO | 2005/073234 A2 | 8/2005 |
| WO | 2009/145814 A2 | 12/2009 |
| WO | 2010/065275 A1 | 6/2010 |
| WO | 2011/147809 A1 | 12/2011 |
| WO | 2011/149921 A1 | 12/2011 |
| WO | 2011/161099 A1 | 12/2011 |
| WO | 2012/004258 A1 | 1/2012 |
| WO | 2012/028647 A1 | 3/2012 |
| WO | 2012/143510 A1 | 10/2012 |
| WO | 2012/152629 A1 | 11/2012 |
| WO | 2013/030138 A1 | 3/2013 |
| WO | 2013/030288 A1 | 3/2013 |

OTHER PUBLICATIONS

WebMd. The Heart and Vascular Disease. (2016) Web. <http://www.webmd.com/heart-disease/vascular-disease>.*
WebMd. Understanding Kidney Disease-Prevention. (2015). Web. <http://www.webmd.com/a-to-z-guides/understanding-kidney-disease-prevention>.*
WebMd. How to Prevent DVT. (2016) Web. <http://www.webmd.com/dvt/deep-vein-thrombosis-prevent-dvt>.*
Mayoclinic. Pulmonary Fibrosis. Treatment and drugs. (2016). Web. <http://www.mayoclinic.org/diseases-conditions/pulmonary-fibrosis/basics/treatment/con-20029091>.*
Dumitrascu et al., "Activation of Soluble Guanylate Cyclase Reverses Experimental Pulmonary Hypertension and Vascular Remodeling," 113(2) Circulation 286, 286-95 (Jan. 2006).
Hobbs, "Soluble guanylate cyclase: an old therapeutic target revisited," 136 British J. Pharmacology 637, 637-40 (2002).
T.A. Michel, "Treatment of Myocardial Ischemia," in Goodman & Gilman's: The Pharmacological Basis of Therapeutics, 823-844 (L.L. Brunton et al., eds. 11th ed., 2006).
Poulos, "Soluble Guanylate Cyclase," Current Opinion in Structural Biology, 736-743 (2006).
Badesch et al., "Prostanoid Therapy for Pulmonary Arterial Hypertension," Journal of the American College of Cardiology, (Jun. 16, 2004), vol. 43, No. 12 Suppl S, pp. 56s-61s.
Banholzer et al., "277. Zum Mechanismus der Thermischen Decarbonylierung von Oxalessigestern," Helvetica Chimica Acta, (1959), vol. 42, No. 277, pp. 2584-2597.
Becker et al., "NO-independent regulatory site of direct sGC stimulators like YC-1 and BAY 41/2272," BMC Pharmacology, (Dec. 28, 2001), vol. 1, No. 13, pp. 1-12.
Cheng et al., "Potential Purine Antagonists VII. Synthesis of 6-Alkylpyrazolo-[3,4-d]pyrimidines," The Journal of Organic Chemistry, (Feb. 1958), vol. 23, No. 2, pp. 191-200.
Daley et al., "The First Complete Identification of a Diastereomeric Catalyst-Substrate (Alkoxide) Species in an Enantioselective Ketone Hydrogenation. Mechanistic Investigations," Journal of the American Chemical Society, (Mar. 16, 2002), vol. 124, No. 14, pp. 3680-3691.
Dermer, "Another Anniversary for the War on Cancer," Nature Biotechnology, (1994), vol. 12, pp. 320.

Evgenov et al., "NO-independent stimulators and activators of soluble guanylate cyclase: discovery and therapeutic potential," Nature Reviews Drug Discovery, (Sep. 2006), vol. 5, No. 9, pp. 755-768.
Freshney, "Culture of Animal Cells," A Manual of Basic Technique, Alan R. Liss Inc., (1983), New York, (7 pages).
Glass et al., "Stimulation of Human Platelet Guanylate Cyclase by Fatty Acids," The Journal of Biological Chemistry, (Feb. 25, 1977), vol. 252, No. 4, pp. 1279-1285.
Greene et al., "The Role of Protective Groups in Organic Synthesis," Greene's Protective Groups in Organic Synthesis, Fourth Edition, (2007), pp. 1-15.
Ghofrani et al., "Soluble Guanylate Cyclase Stimulation: an Emerging Option in Pulmonary Hypertension Therapy," European Respiratory Review, (2009), vol. 18, No. 11, pp. 35-41.
Grassetti et al., "Synthesis of Some Homologs of Fluoropyruvic Acid and Their Effect on the Carbohydrate Metabolism of Ehrlich Ascites Tumor and on Lactate Dehydrogenase," J. Med. Chem., (Jan. 1966), vol. 9, No. 1, pp. 149-151.
Hassan et al., "Aryl-Aryl Bond Formation One Century after the Discovery of the Ullmann Reaction," Chemical Reviews, (Mar. 8, 2002), vol. 102, No. 5, pp. 1359-1470.
Herdemann et al., "Identification of Potent ITK Inhibitors Through Focused Compound Library Design Including Structural Information," Bioorganic & Medicinal Chemistry Letters, (Dec. 1, 2010), vol. 20, No. 23, pp. 6998-7003.
Hughes, "Progress in the Mitsunobu Reaction. A Review," Organic Preparations and Procedures Int., (1996), vol. 28, No. 2, pp. 127-164.
Kelley et al., "Synthesis and Anticonvulsant Activity of N-Benzylpyrrolo[2,3-d]-, -pyrazolo[3,4-d]-, and -triazolo[4,5-d]pyrimidines: Imidazole Ring-Modified Analogues of 9-(2-Fluorobenzyl)-6-(methylamino)-9H-purin," Journal of Medicinal Chemistry, (Sep. 1995), vol. 38, No. 19, pp. 3884-3888.
Ko et al., "YC-1, a Novel Activator of Platelet Guanylate Cyclase," Blood, (Dec. 15, 1994), vol. 84, No. 12, pp. 4226-4233.
Kozo et al., "Spontaneous Hypertension in Rats," Int Rev. Exp. Pathol, (1969), vol. 7, pp. 227-270.
Mittendorf et al., "Discovery of Riociguat (BAY 63/2521): A Potent, Oral Stimulator of Soluble Guanylate Cyclase for the Treatment of Pulmonary Hypertension," ChemMedChem, (May 2009), vol. 4, No. 5, pp. 853-865.
Mulsch et al., "Effect of YC-1, an NO-independent, Superoxide-Sensitive Stimulator of Soluble Guanylyl Cyclase, on Smooth Muscle Responsiveness to Nitrovasodilators," British Journal of Pharmacology, (Feb. 1997), vol. 120, No. 4, pp. 681-689.
Olah et al., "Synthesis and Investigation of Organic Fluorine Compounds. XXIII. Preparation of Aromatic Fluorinated Esters as Local Anesthetics" The Journal of Organic Chemistry, (Aug. 1957), vol. 22, No. 8, pp. 879-881.
Oudot et al., "Combination of BAY 60/4552 and Vardenafil Exerts Proerectile Facillitator Effects in Rats with Cavernous Nerve Injury: A Proof of Concept Study for the Treatment of Phosphodiesterase Type 5 Inhibitor Failure," European Urology, (Nov. 2011), vol. 60, No. 5, pp. 1020-1026.
Palacios et al., "A New and Efficient Synthesis of Imidazo[1,5-a]pyridine Derivatives by a Tandem Aza-Wittig / Electrocyclic Ring Closure of N-vinylic phosphazenes," Tetrahedron, (Mar. 20, 1995), vol. 51, No. 12, pp. 3683-3690.
Pettibone et al., "A Structurally Novel Stimulator of Guanylate Cyclase with Long-Lasting Hypotensive Activity in the Dog," European Journal of Pharmacology, (Oct. 22, 1985), vol. 116, No. 3, pp. 307-312.
Reichardt et al., "Darstellung von Fluor- and Jodmalondialdehyd," Liebigs Ann. Chem. (1970), 737, pp. 99-107.
Robins, "Potential Purine Antagonists. I. Synthesis of Some 4,B-Substituted Pyrazolo [3,4-d] pyrimidines," Journal of the American Chemical Society, (Feb. 1956), vol. 78, No. 4, pp. 784-790.
Rocaboy et al., "Syntheses and Reactivities of Disubstituted and Trisubstituted Fluorous Pyridines with High Fluorous Phase Affinities: Solid State, Liquid Crystal, and Ionic Liquid-Phase Properties," The Journal of Organic Chemistry, (Oct. 4, 2002), vol. 67, No. 20, pp. 6863-6870.

(56) References Cited

OTHER PUBLICATIONS

Saenz De Tejada et al., "The Phosphodiesterase Inhibitory Selectivity and the in Vitro and in Vivo Potency of the new PDE5 Inhibitor Vardenafil," International Journal of Impotence Research, (Oct. 2001), vol. 13, No. 5, pp. 282-290.

Sard et al., "Preparation of 4,5-Disubstituted Pyrimidines: Ring Substitution of 5-Mesyloxymethylpyrimidines," The Journal of Organic Chemistry, (Nov. 22, 2000), vol. 65, No. 26, pp. 9261-9264.

Sharkovska et al., "Nitric oxide-independent stimulation of soluble guanylate cyclase reduces organ damage in experimental low-renin and high-renin models," Journal of Hypertension, (Aug. 2010), vol. 28, No. 8, pp. 1666-1675.

Stasch et al., "Soluble Guanylate Cyclase as an Emerging Therapeutic Target in Cardiopulmonary Disease," Circulation, (May 24, 2011), vol. 123, No. 20, pp. 2263-2273.

Straub et al., "NO-Independent Stimulators of Soluble Guanylate Cyclase," Bioorganic & Medicinal Chemistry Letters, (Mar. 26, 2011), vol. 11, Issue 6, pp. 781-784.

Toche et al., "Synthesis of Pyrazolopyridine 3-Carboxylates by Friedlander Condensation," Journal of Heterocyclic Chemistry, (Mar. 2010), vol. 47, No. 2, pp. 287-291.

Tyutin et al., "Synthesis of Esters of 3, 3-Dicyano-2-(Trifluoromethyl) Acrylic Acid and Their Reactions with Arylamines," Journal of Fluorine Chemistry, (Mar. 1991), vol. 51, Issue 3, pp. 323-334.

Van Den Buuse, "Circadian Rhythms of Blood Pressure, Heart Rate, and Locomotor Activity in Spontaneously Hypertensive Rats as Measured With Radio-Telemetry," Physiology & Behavior, (Apr. 1994), vol. 55, No. 4, pp. 783-787.

Wilson et al., "Development of a Scaleable Synthesis of a Partial Nicotinic Acid Receptor Agonist," Organic Process Research & Development, (Mar. 16, 2009), vol. 13, No. 3, pp. 543-547.

Winn et al., "2-(Alkylamino) Nicotinic Acid and Analogs. Potent Angiotensin II Antagonists," Journal of Medicinal Chemistry, (Sep. 1993), vol. 36, No. 18, pp. 2676-2688.

Witte et al., "Experimental heart failure in rats: effects on cardiovascular circadian rhythms and on myocardial β-adrenergic signaling," Cardiovascular Research, (Aug. 2000), vol. 47, No. 2, pp. 350-358.

Wunder et al., "A cell-based cGMP assay useful for ultra-high-throughput screening and identification of modulators of the nitric oxide/cGMP pathway," Analytical Biochemistry, (Apr. 1, 2005), vol. 339, No. 1, pp. 104-112.

Wu et al., "YC-1 Inhibited Human Platelet Aggregation Through NO-Independent Activation of Soluble Guanylate Cyclase," British Journal of Pharmacology, (Oct. 1995), vol. 116, No. 3, pp. 1973-1978.

Yu et al., "Vasorelaxant Effect of Isoliquiritigenin, a Novel Soluble Guanylate Cyclase Activator, in Rat Aorta," British Journal of Pharmacology, (Apr. 1995), vol. 114, No. 8, pp. 1587-1594.

Wunder et al., "Characterization of the First Potent and Selective PDE9 Inhibitor Using a cGMP Reporter Cell Line," Molecular Pharmacology 2005, vol. 68, No. 6, 1775-1781.

International Search Report issued on Jul. 26, 2013, by the European Patent Office as the International Searching Authority in corresponding International Application No. PCT/EP2013/054427. (9 pages).

International Preliminary Report on Patentability (Form PCT/IB/373) and the Written Opinion of the International Searching Authority (Form PCT/ISA/237) issued on Sep. 9, 2014, in corresponding International Application No. PCT/EP2013/054427. (22 pages).

Follmann et al., U.S. Appl. No. 14/371,054 entitled "Substituted Triazine Derivatives and Use Thereof as Stimulators of Soluble Guanylate Cyclase" filed Jul. 8, 2014.

* cited by examiner

SUBSTITUTED AZABICYCLES AND USE THEREOF

The present application relates to novel substituted azabicycles, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO can bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, arteriosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem.

In addition to the side effects, the development of tolerance is one of the crucial disadvantages of this mode of treatment.

In recent years, some substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mülsch et al., Brit. J. Pharmacol. 120 (1997), 681], fatty acids [Goldberg et al., J. Biol. Chem. 252 (1977), 1279], diphenyliodonium hexafluorophosphate [Pettibone et al., Eur. J. Pharmacol. 116 (1985), 307], isoliquiritigenin [Yu et al., Brit. J. Pharmacol. 114 (1995), 1587] and various substituted pyrazole derivatives (WO 98/16223).

As stimulators of soluble guanylate cyclase, WO 00/06569 discloses fused pyrazole derivatives, and WO 01/083490 a fused aminopyridine derivative. WO 2010/065275 discloses pyrrolopyrimidones as activators of soluble guanylate cyclase.

It was an object of the present invention to provide novel substances which act as stimulators of soluble guanylate cyclase and which have an identical or improved therapeutic profile compared to the compounds known from the prior art, for example with respect to their in vivo properties such as their pharmacokinetic and pharmacodynamic behaviour and/or their metabolic profile and/or their dose-effect relationship.

The present invention provides compounds of the general formula (I)

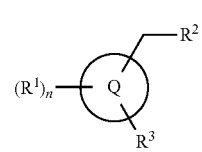

in which
the ring Q represents 8- or 9-membered heteroaryl,
$R^1$ represents fluorine, chlorine, cyano, difluoromethyl, trifluoromethyl, ($C_1$-$C_4$)-alkyl, ($C_3$-$C_7$)-cycloalkyl or ($C_1$-$C_4$)-alkoxy,
n represents a number 0, 1 or 2,
$R^2$ represents trifluoromethyl, ($C_1$-$C_6$)-alkyl, ($C_3$-$C_8$)-cycloalkyl, phenyl or 5- or 6-membered heteroaryl,
  where ($C_1$-$C_6$)-alkyl is substituted by a substituent selected from the group consisting of difluoromethyl and trifluoromethyl,
  where ($C_1$-$C_6$)-alkyl may be substituted by 1 to 3 fluorine substituents,
  where ($C_3$-$C_8$)-cycloalkyl may be substituted by 1 or 2 substituents independently of one another selected from the group consisting of fluorine, methyl and methoxy,
  where phenyl is substituted by 1 to 3 fluorine substituents,
  where phenyl may be substituted by 1 or 2 substituents independently of one another selected from the group consisting of methyl and methoxy,
  and
  where 5- and 6-membered heteroaryl may be substituted by 1 or 2 substituents selected independently of one another from the group consisting of fluorine, trifluoromethyl and methyl,
$R^3$ represents a group of the formula

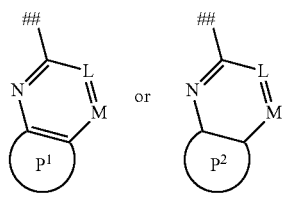

where
## represents the point of attachment to the ring Q,
L represents CH or N,
M represents $CR^4$ or N, in which
$R^4$ represents —$R^5$, —$OR^6$ or —$NR^7R^8$,
in which
$R^5$ represents hydrogen, halogen, cyano, $(C_1\text{-}C_6)$-alkyl, $(C_2\text{-}C_4)$-alkynyl, $(C_1\text{-}C_4)$-alkylcarbonyl or $(C_1\text{-}C_4)$-alkoxycarbonyl,
in which $(C_1\text{-}C_6)$-alkyl and $(C_2\text{-}C_4)$-alkynyl for their part may be substituted by 1 or 2 substituents independently of one another selected from the group consisting of fluorine, difluoromethyl, trifluoromethyl, $(C_1\text{-}C_6)$-alkyl, $(C_3\text{-}C_6)$-cycloalkyl, difluoromethoxy, trifluoromethoxy, oxo —(C=O)$_p$—OR$^9$, —C(=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$ and —SO$_2$—NR$^9$R$^{10}$,
$R^6$ represents hydrogen, $(C_1\text{-}C_6)$-alkyl, $(C_3\text{-}C_7)$-cycloalkyl, 4- to 7-membered heterocyclyl, phenyl or 5- or 6-membered heteroaryl,
in which $(C_1\text{-}C_6)$-alkyl, $(C_3\text{-}C_7)$-cycloalkyl, 4- to 7-membered heterocyclyl, phenyl or 5- or 6-membered heteroaryl may be substituted by 1 to 3 substituents independently of one another selected from the group consisting of fluorine, difluoromethyl, trifluoromethyl, $(C_1\text{-}C_6)$-alkyl, $(C_3\text{-}C_6)$-cycloalkyl, difluoromethoxy, trifluoromethoxy, oxo —(C=O)$_p$—OR$^9$, —C(=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$ and —SO$_2$—NR$^9$R$^{10}$,
$R^7$ represents hydrogen or $(C_1\text{-}C_4)$-alkyl,
$R^8$ represents hydrogen, $(C_1\text{-}C_6)$-alkyl, $(C_3\text{-}C_7)$-cycloalkyl, 4- to 7-membered heterocyclyl, phenyl or 5- or 6-membered heteroaryl,
in which $(C_1\text{-}C_6)$-alkyl, $(C_3\text{-}C_7)$-cycloalkyl, 4- to 7-membered heterocyclyl, phenyl or 5- or 6-membered heteroaryl may be substituted by 1 to 3 substituents independently of one another selected from the group consisting of fluorine, difluoromethyl, trifluoromethyl, $(C_1\text{-}C_6)$-alkyl, $(C_3\text{-}C_7)$-cycloalkyl, difluoromethoxy, trifluoromethoxy, oxo, —(C=O)$_p$—OR$^9$, —(C=O)$_p$—NR$^9$R$^{10}$, —NR$^9$—(C=O)—R$^{10}$, —NR$^9$—(C=O)—OR$^{10}$, —NR$^9$—(C=O)—NR$^{10}$R$^{11}$, —NR$^9$—SO$_2$—R$^{10}$, —S(O)$_q$—R$^{12}$, —SO$_2$—NR$^9$R$^{10}$, phenyl, 4- to 7-membered heterocyclyl and 5- or 6-membered heteroaryl,
in which in each case
p represents the number 0 or 1,
q represents the number 0, 1 or 2,
$R^9$, $R^{10}$ and $R^{11}$ independently of one another each represent hydrogen, $(C_1\text{-}C_6)$-alkyl or $(C_3\text{-}C_8)$-cycloalkyl,
in which $(C_1\text{-}C_6)$-alkyl for its part may be substituted by 1 or 2 substituents independently of one another selected from the group consisting of fluorine, difluoromethyl, trifluoromethyl, hydroxy, $(C_1\text{-}C_6)$-alkoxy, difluoromethoxy, trifluoromethoxy, $(C_1\text{-}C_6)$-alkoxycarbonyl, amino, mono-$(C_1\text{-}C_6)$-alkylamino, di-$(C_1\text{-}C_6)$-alkylamino and 4- to 7-membered heterocyclyl,
or
$R^9$ and $R^{10}$ together with the atom(s) to which they are respectively attached form a 4- to 7-membered heterocycle,
in which the 4- to 7-membered heterocycle for its part may be substituted by 1 or 2 substituents independently of one another selected from the group consisting of fluorine, cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
or
$R^{10}$ and $R^{11}$ together with the atom(s) to which they are respectively attached form a 4- to 7-membered heterocycle,
in which the 4- to 7-membered heterocycle for its part may be substituted by 1 or 2 substituents independently of one another selected from the group consisting of fluorine, cyano, trifluoromethyl, $(C_1\text{-}C_6)$-alkyl, hydroxy, oxo, $(C_1\text{-}C_6)$-alkoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
and in which
$R^{12}$ represents $(C_1\text{-}C_6)$-alkyl or $(C_3\text{-}C_7)$-cycloalkyl,
or in which
$R^7$ and $R^8$ together with the nitrogen atom to which they are attached form a 4- to 7-membered heterocycle or 5- or 6-membered heteroaryl,
in which the 4- to 7-membered heterocycle and the 5- or 6-membered heteroaryl may be substituted by 1 to 3 substituents independently of one another selected from the group consisting of fluorine, cyano, difluoromethyl, trifluoromethyl, $(C_1\text{-}C_6)$-alkyl, $(C_3\text{-}C_7)$-cycloalkyl, hydroxy, oxo, $(C_1\text{-}C_6)$-alkoxy, difluoromethoxy, trifluoromethoxy, $(C_1\text{-}C_6)$-alkoxycarbonyl, amino, mono-$(C_1\text{-}C_6)$-alkylamino and di-$(C_1\text{-}C_6)$-alkylamino,
and
in which all $(C_1\text{-}C_4)$-alkyl, $(C_1\text{-}C_6)$-alkyl, $(C_3\text{-}C_8)$-cycloalkyl and 4- to 7-membered heterocyclyl groups mentioned above, unless stated otherwise, may each independently of one another additionally be substituted by 1 to 3 substituents independently of one another selected from the group consisting of fluorine, difluoromethyl, trifluoromethyl, $(C_3\text{-}C_7)$-cycloalkyl, hydroxy, difluoromethoxy, trifluoromethoxy, $(C_1\text{-}C_4)$-alkoxy, hydroxycarbonyl, $(C_1\text{-}C_4)$-alkoxycarbonyl, amino, phenyl, 4- to 7-membered heterocyclyl and 5- or 6-membered heteroaryl,
the ring $P^1$ represents 5- to 7-membered heterocyclyl, phenyl or 5- or 6-membered heteroaryl,
in which 5- to 7-membered heterocyclyl, phenyl and 5- or 6-membered heteroaryl may be substituted by 1 to 3 substituents independently of one another selected from the group consisting of halogen, cyano, difluoromethyl, trifluoromethyl, trideuteromethyl, $(C_1\text{-}C_6)$-alkyl, $(C_2\text{-}C_6)$-alkenyl, $(C_3\text{-}C_7)$-cycloalkyl, oxo, difluoromethoxy, trifluoromethoxy, thiooxo and a group of the formula -M-R$^{13}$,
in which $(C_1\text{-}C_6)$-alkyl may be substituted by 1 to 3 substituents selected independently of one another from the group consisting of fluorine, cyano, trifluoromethyl, $(C_3\text{-}C_7)$-cycloalkyl, difluoromethoxy and trifluoromethoxy,
the ring $P^2$ represents 5-membered heteroaryl,
in which 5-membered heteroaryl may be substituted by 1 to 3 substituents independently of one another selected from the group consisting of halogen, cyano, difluoromethyl, trifluoromethyl, trideuteromethyl, ($C_1$-$C_6$)-alkyl, ($C_2$-$C_6$)-alkenyl, ($C_3$-$C_7$)-cycloalkyl, oxo, difluoromethoxy, trifluoromethoxy, thiooxo and a group of the formula -M-$R^{13}$,
in which ($C_1$-$C_6$)-alkyl may be substituted by 1 to 3 substituents selected independently of one another from the group consisting of fluorine, cyano, trifluoromethyl, ($C_3$-$C_7$)-cycloalkyl, difluoromethoxy and trifluoromethoxy,
and in which in each case
M represents a bond or ($C_1$-$C_4$)-alkanediyl,
$R^{13}$ represents —(C=O)$_r$—O$R^{14}$, —(C=O)$_r$—N$R^{14}R^{15}$, —C(=S)—N$R^{14}R^{15}$, —N$R^{14}$—(C=O)—$R^{15}$, —N$R^{14}$—(C=O)—O$R^{17}$, —N$R^{14}$—(C=O)—N$R^{15}R^{16}$, —N$R^{14}$—SO$_2$—N$R^{15}R^{16}$, —N$R^{14}$—SO$_2$—$R^{17}$, —S(O)$_s$—$R^{17}$, —SO$_2$—N$R^{14}R^{15}$, 4- to 7-membered heterocyclyl, phenyl, benzyl or 5- or 6-membered heteroaryl,
in which
r represents the number 0 or 1,
s represents the number 0, 1 or 2,
$R^{14}$, $R^{15}$ and $R^{16}$ independently of one another each represent hydrogen, ($C_1$-$C_6$)-alkyl, ($C_3$-$C_8$)-cycloalkyl, 4- to 7-membered heterocyclyl, phenyl, benzyl or 5- or 6-membered heteroaryl,
or
$R^{14}$ and $R^{15}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, ($C_1$-$C_6$)-alkyl, hydroxy, oxo, ($C_1$-$C_6$)-alkoxy, trifluoromethoxy, ($C_1$-$C_6$)-alkoxycarbonyl, amino, mono-($C_1$-$C_6$)-alkylamino and di-($C_1$-$C_6$)-alkylamino,
or
$R^{14}$ and $R^{15}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, ($C_1$-$C_6$)-alkyl, hydroxy, oxo, ($C_1$-$C_6$)-alkoxy, trifluoromethoxy, ($C_1$-$C_6$)-alkoxycarbonyl, amino, mono-($C_1$-$C_6$)-alkylamino and di-($C_1$-$C_6$)-alkylamino,
$R^{17}$ represents ($C_1$-$C_6$)-alkyl or ($C_3$-$C_7$)-cycloalkyl,
or
$R^{14}$ and $R^{17}$ together with the atom(s) to which they are respectively attached form a 4- to 7-membered heterocycle,
in which the 4- to 7-membered heterocycle for its part may be substituted by 1 or 2 substituents independently of one another selected from the group consisting of cyano, trifluoromethyl, ($C_1$-$C_6$)-alkyl, hydroxy, oxo, ($C_1$-$C_6$)-alkoxy, trifluoromethoxy, ($C_1$-$C_6$)-alkoxycarbonyl, amino, mono-($C_1$-$C_6$)-alkylamino and di-($C_1$-$C_6$)-alkylamino,
and
in which 4- to 7-membered heterocyclyl, phenyl, benzyl and 5- or 6-membered heteroaryl for their part may be substituted by 1 to 3 substituents independently of one another selected from the group consisting of halogen, cyano, difluoromethyl, trifluoromethyl, ($C_1$-$C_6$)-alkyl, ($C_3$-$C_7$)-cycloalkyl, hydroxy, oxo, thioxo and ($C_1$-$C_4$)-alkoxy,
and
in which the ($C_1$-$C_4$)-alkyl, ($C_1$-$C_6$)-alkyl, ($C_3$-$C_8$)-cycloalkyl and 4- to 7-membered heterocyclyl groups mentioned above, unless stated otherwise, may each independently of one another additionally be substituted by 1 to 3 substituents independently of one another selected from the group consisting of fluorine, difluoromethyl, trifluoromethyl, ($C_1$-$C_6$)-alkyl, ($C_3$-$C_7$)-cycloalkyl, hydroxy, difluoromethoxy, trifluoromethoxy, ($C_1$-$C_4$)-alkoxy, hydroxycarbonyl, ($C_1$-$C_4$)-alkoxycarbonyl, amino, phenyl, 4- to 7-membered heterocyclyl and 5- or 6-membered heteroaryl,
and the N-oxides, salts, solvates, salts of the N-oxides and solvates of the N-oxides or salts thereof,
except for the compounds:
2-[1-(2-fluorobenzyl)-1H-pyrazolo[3,4-b]pyridin-3-yl]-8-methyl-9H-purine,
2-[1-(2-fluorobenzyl)-1H-pyrazolo[3,4-b]pyridin-3-yl]-8-methyl-9H-purine-6-amine,
N-butyl-2-[1-(2-fluorobenzyl)-1H-pyrazolo[3,4-b]pyridin-3-yl]-8-methyl-9H-purine-6-amine.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as working examples, and their salts, solvates and solvates of the salts, if the compounds, comprised by formula (I), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of solvates in which the coordination is with water. Preferred solvates in the context of the present invention are hydrates.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the substituents, unless specified otherwise, are each defined as follows:

Alkyl in the context of the invention is a straight-chain or branched alkyl radical having the number of carbon atoms specified in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl or carbocycle in the context of the invention is a monocyclic saturated alkyl radical having the number of carbon atoms specified in each case. The following may be mentioned by way of example and by way of preference: cyclopropyl, cyclobutyl, cyclopentyl, cyclohexyl and cycloheptyl.

5- to 7-membered saturated or partly unsaturated carbocycle in the context of the present invention is a saturated or partly unsaturated cyclic alkyl radical having the number of carbon atoms specified in each case. The following may be mentioned by way of example and by way of preference: cyclopentyl, cyclohexyl, cycloheptyl, cyclopentenyl, cyclohexenyl and cycloheptenyl.

Alkanediyl in the context of the invention is a straight-chain or branched divalent alkyl radical having 1 to 4 carbon atoms. The following may be mentioned by way of example and by way of preference: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl and butane-2,3-diyl. Preference is given to: methylene, ethane-1,2-diyl, propane-1,3-diyl and butane-1,4-diyl.

Alkenyl in the context of the invention is a straight-chain or branched alkenyl radical having 2 to 6 or 2 to 4 carbon atoms and a double bond. The following may be mentioned by way of example and by way of preference: vinyl, allyl, isopropenyl and n-but-2-en-1-yl.

Alkynyl in the context of the invention is a straight-chain or branched alkynyl radical having 2 to 4 carbon atoms and one triple bond. The following may be mentioned by way of example and by way of preference: ethynyl, n-prop-1-yn-1-yl, n-prop-2-yn-1-yl, n-but-2-yn-1-yl and n-but-3-yn-1-yl.

Alkoxy in the context of the invention is a straight-chain or branched alkoxy radical having 1 to 6 or 1 to 4 carbon atoms. The following may be mentioned by way of example: methoxy, ethoxy, n-propoxy, isopropoxy, 1-methylpropoxy, n-butoxy, iso-butoxy, tert-butoxy, n-pentoxy, isopentoxy, 1-ethylpropoxy, 1-methylbutoxy, 2-methylbutoxy, 3-methylbutoxy and n-hexoxy. Preference is given to a linear or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Alkylcarbonyl in the context of the invention is a linear or branched alkyl radical having 1 to 6 or 1 to 4 carbon atoms and a carbonyl group attached in the 1 position. The following may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

Alkoxycarbonyl in the context of the invention is a straight-chain or branched alkoxy radical having 1 to 6 or 1 to 4 carbon atoms and a carbonyl group attached to the oxygen. The following may be mentioned by way of example and by way of preference: methoxycarbonyl, ethoxycarbonyl, n-propoxycarbonyl, isopropoxycarbonyl and tert-butoxycarbonyl.

Monoalkylamino in the context of the invention is an amino group having a straight-chain or branched alkyl substituent having 1 to 6 carbon atoms. The following may be mentioned by way of example and by way of preference: methylamino, ethylamino, n-propylamino, isopropylamino and tert-butylamino.

Dialkylamino in the context of the invention is an amino group having two identical or different, straight-chain or branched alkyl substituents each having 1 to 6 carbon atoms. The following may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

5- to 7-membered saturated or partly unsaturated heterocycle in the context of the invention is a saturated or partly unsaturated heterocycle which has a total of 5 to 7 ring atoms and contains one ring heteroatom from the group of N, O, S, SO and/or $SO_2$. The following may be mentioned by way of example: pyrrolidinyl, tetrahydrofuranyl, piperidinyl, tetrahydropyranyl, dihydropyrrolyl, dihydropyridyl.

Heterocyclyl or heterocycle in the context of the invention is a saturated heterocycle which has a total of 4 to 7 ring atoms and contains one or two ring heteroatoms from the group consisting of N, O, S, SO and/or $SO_2$. The following may be mentioned by way of example: azetidinyl, oxetanyl, pyrrolidinyl, pyrazolidinyl, imidazolinyl, tetrahydrofuranyl, piperidinyl, piperazinyl, tetrahydropyranyl, morpholinyl, thiomorpholinyl and dioxidothiomorpholinyl. Preference is given to azetidinyl, oxetanyl, pyrrolidinyl, tetrahydrofuranyl, piperidinyl, tetrahydropyranyl and morpholinyl.

5- or 6-membered heteroaryl in the context of the invention is a monocyclic aromatic heterocycle (heteroaromatic) which has a total of 5 or 6 ring atoms, contains up to three identical or different ring heteroatoms from the group consisting of N, O and/or S and is attached via a ring carbon atom or optionally via a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyrazolyl, oxazolyl, thiazolyl, triazolyl, oxadiazolyl, thiadiazolyl, pyridyl and pyrimidinyl.

8- or 9-membered heteroaryl in the context of the invention is a bicyclic aromatic or partly unsaturated heterocycle which has a total of 8 or 9 ring atoms and contains at least two nitrogen atoms and up to two further, identical or different ring heteroatoms from the group of N, O and/or S. The following may be mentioned by way of example: dihydrothienopyrazolyl, thienopyrazolyl, pyrazolopyrazolyl, imidazothiazolyl, tetrahydrocyclopentapyrazolyl, dihydrocyclopentapyrazolyl, tetrahydroindazolyl, dihydroindazolyl, indazolyl, pyrazolopyridinyl, tetrahydropyrazolopyridinyl, pyrazolopyrimidinyl, imidazopyridinyl and imidazopyridazinyl.

Halogen in the context of the invention is fluorine, chlorine, bromine and iodine. Preference is given to fluorine and chlorine.

An oxo group in the context of the invention is an oxygen atom attached to a carbon atom via a double bond.

A thiooxo group in the context of the invention is a sulphur atom attached via a double bond to a carbon atom.

In the formula of the group that Q or $R^3$ may represent, the end point of the line marked by the symbol *, ** or ## does not represent a carbon atom or a $CH_2$ group but is part of the bond to the respective atom to which Q or $R^3$ is attached.

If radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

Preference is given in the context of the present invention to compounds of the formula (I) in which the ring Q represents a group of the formula

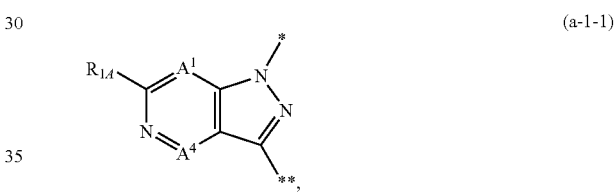
(a-1-1)

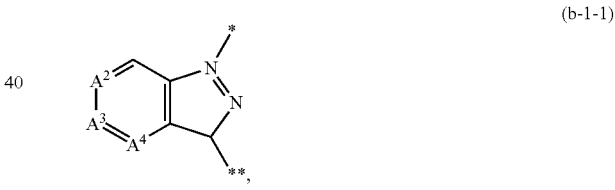
(b-1-1)

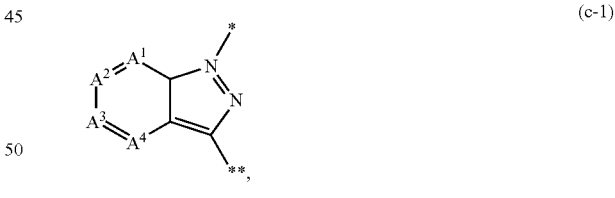
(c-1)

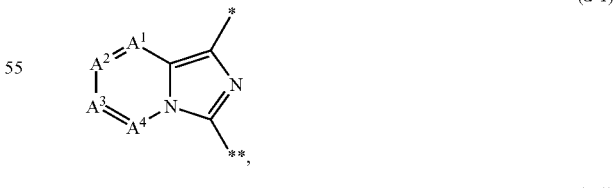
(d-1)

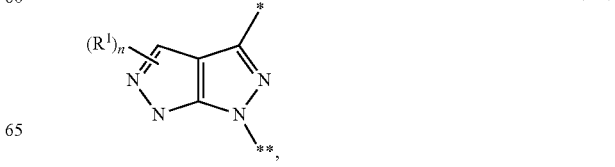
(e-1)

-continued (f-1)
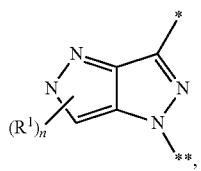

(g-1)
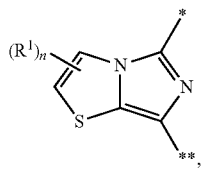

(h-1)
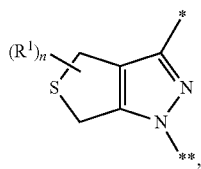

(i-1)
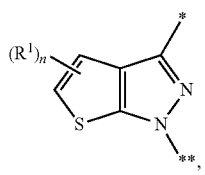

(j-1)
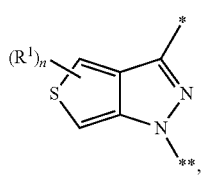

(k-1)
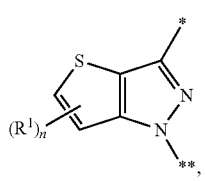

(l-1)
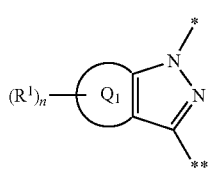

(m-1)
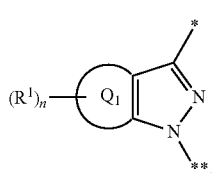

(n-1)
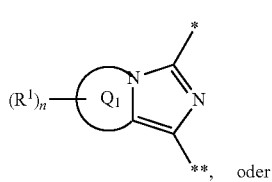, oder (o-1)
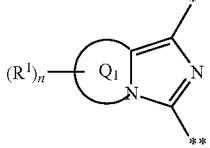

where

* represents the point of attachment to —CH$_2$—R$^2$,

** represents the point of attachment to R$^3$, the ring Q$_1$ together with the atoms to which it is attached forms a 5- to 7-membered saturated or partially unsaturated carbocycle or a 5- to 7-membered saturated or partially unsaturated heterocycle, R$^1$ represents fluorine, chlorine, methyl, hydroxy or oxo, R$^{1A}$ represents hydrogen or methyl, n represents a number 0, 1 or 2, A$^1$, A$^2$, A$^3$ and A$^4$ independently of one another each represent N, CH or CR$^1$, with the proviso that not more than two of the A$^1$, A$^2$, A$^3$ and A$^4$ groups represent N, R$^2$ represents trifluoromethyl, 2,2,2-trifluoroethyl, 3,3,3-trifluoroprop-1-yl, 2,2,3,3-tetrafluorprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl, where phenyl is substituted by 1 to 3 fluorine substituents, and where cyclopropyl, cyclobutyl, cyclopentyl, cyclohexyl, pyridyl, pyrimidinyl, pyrazinyl and pyridazinyl may be substituted by 1 or 2 fluorine substituents, R$^3$ represents a group of the formula

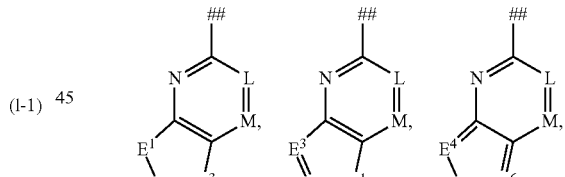

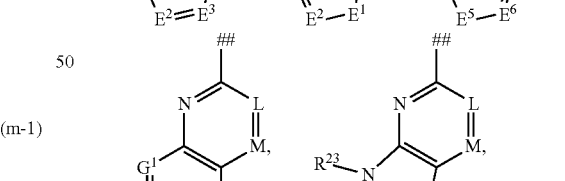

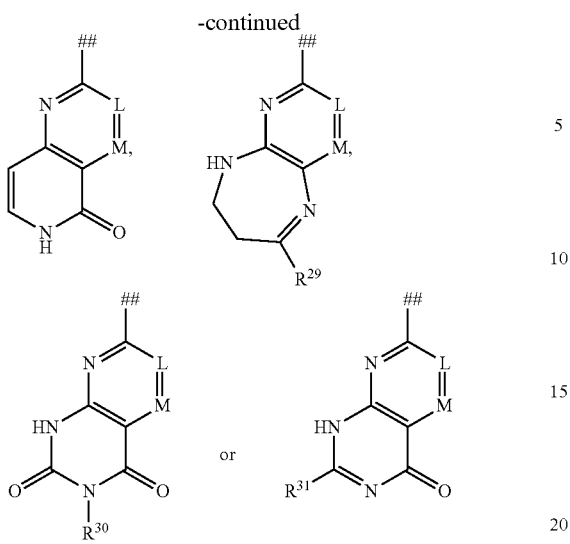

where
## represents the point of attachment to the ring Q,
L represents CH or N,
M represents $CR^4$ or N,
  in which
    $R^4$ represents —$R^5$, —$OR^6$ or —$NR^7R^8$,
    in which
      $R^5$ represents hydrogen, chlorine, cyano, ($C_1$-$C_4$)-alkyl or ($C_2$-$C_4$)-alkynyl,
        in which ($C_1$-$C_4$)-alkyl and ($C_2$-$C_4$)-alkynyl for their part may be substituted by 1 or 2 substituents independently of one another selected from the group consisting of fluorine, difluoromethyl, trifluoromethyl, cyclopropyl, cyclobutyl, cyclopentyl, difluoromethoxy, trifluoromethoxy, —(C=O)$_p$—$OR^9$ and —C(=O)$_p$—$NR^9R^{10}$,
        in which
          p represents the number 0,
          $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
          or
          $R^9$ and $R^{10}$ together with the atom(s) to which they are respectively attached form an azetidinyl, pyrrolidinyl, piperidinyl, piperazinyl or morpholinyl ring,
            in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
      $R^6$ represents ($C_1$-$C_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
        in which ($C_1$-$C_6$)-alkyl may be substituted by 1 to 3 substituents independently of one another selected from the group consisting of fluorine, difluoromethyl, trifluoromethyl, cyclopropyl, cyclobutyl, cyclopentyl, difluoromethoxy, trifluoromethoxy, —(C=O)$_p$—$OR^9$, —(C=O)$_p$—$NR^9R^{10}$ and —$NR^9$—(C=O)—$R^{10}$,
        and
        in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl may be substituted by 1 to 3 substituents independently of one another selected from the group consisting of fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—$OR^9$ and —(C=O)$_p$—$NR^9R^{10}$,
        in which in each case
          p represents the number 0 or 1,
          $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
          or
          $R^9$ and $R^{10}$ together with the atom(s) to which they are respectively attached form an azetidinyl, pyrrolidinyl, piperidinyl, piperazinyl or morpholinyl ring,
            in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
    $R^7$ represents hydrogen, methyl or ethyl,
    $R^8$ represents hydrogen, ($C_1$-$C_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
      in which ($C_1$-$C_6$)-alkyl, cyclopropyl, cyclobutyl and cyclopentyl are substituted by 1 to 3 substituents independently of one another selected from the group consisting of fluorine, difluoromethyl, trifluoromethyl methyl, ethyl, cyclopropyl, cyclobutyl, cyclopentyl, difluoromethoxy, trifluoromethoxy, —(C=O)$_p$—$OR^9$, —(C=O)$_p$—$NR^9R^{10}$, —$NR^9$—(C=O)—$R^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl,
      in which
        p represents the number 0 or 1,
        $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino and in which oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part may be substituted by 1 or 2 substituents independently of one another selected from the group consisting of fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy, and in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl, cyclopropyl, cyclobutyl, cyclopentyl, difluoromethoxy, trifluoromethoxy, oxo, $-(C=O)_p-OR^9$ and $-(C=O)_p-NR^9R^{10}$, in which p represents the number 0 or 1, $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino, or $R^7$ and $R^8$ together with the nitrogen atom to which they are attached form an azetidinyl, pyrrolidinyl, imidazolidinyl, piperidinyl, dihydropiperidinyl, piperazinyl, morpholinyl, pyrazolyl, imidazolyl or triazolyl ring, in which the azetidinyl, pyrrolidinyl, imidazolidinyl, piperidinyl, dihydropiperidinyl, piperazinyl, morpholinyl, pyrazolyl, imidazolyl or triazolyl ring may be substituted by 1 or 2 substituents independently of one another selected from the group consisting of fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $E^1$ represents O, S or $NR^{18}$, in which $R^{18}$ represents hydrogen, trifluoromethyl or ($C_1$-$C_4$)-alkyl, in which ($C_1$-$C_4$)-alkyl for its part may be substituted by 1 or 2 substituents independently of one another selected from the group consisting of fluorine, trifluoromethyl, hydroxy, methoxy and ethoxy, $E^2$ represents N, $E^3$ represents N or $CR^{19}$, in which $R^{19}$ represents hydrogen, fluorine, difluoromethyl, trifluoromethyl, ($C_1$-$C_4$)-alkyl, cyclopropyl, cyclobutyl, cyclopentyl or a group of the formula -M-$R^{13}$, in which ($C_1$-$C_4$)-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents $-(C=O)_r-OR^{14}$, $-(C=O)_r-NR^{14}R^{15}$, $-C(=S)-NR^{14}R^{15}$, $-NR^{14}-(C=O)-OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, $E^4$ and $E^6$ independently of one another each represent N or $CR^{20}$, in which $R^{20}$ represents hydrogen, fluorine, difluoromethyl, trifluoromethyl, $(C_1-C_4)$-alkyl, cyclopropyl, cyclobutyl, cyclopentyl or a group of the formula -M-$R^{13}$, in which $(C_1-C_4)$-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents —(C=O)$_r$—$OR^{14}$, —(C=O)$_r$—$NR^{14}R^{15}$, —C(=S)—$NR^{14}R^{15}$, —$NR^{14}$—(C=O)—$OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, $E^5$ represents $NR^{21}$, in which $R^{21}$ represents hydrogen or $(C_1-C_4)$-alkyl, in which $(C_1-C_4)$-alkyl may itself be substituted by 1 or 2 substituents each independently of one another selected from the group consisting of fluorine, trifluoromethyl, hydroxy, methoxy and ethoxy, $G^1$, $G^2$, $G^3$ and $G^4$ independently of one another each represent N or $CR^{22}$, in which $R^{22}$ represents hydrogen, fluorine, difluoromethyl, trifluoromethyl, $(C_1-C_4)$-alkyl, cyclopropyl, cyclobutyl, cyclopentyl or a group of the formula -M-$R^{13}$, in which $(C_1-C_4)$-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents —(C=O)$_r$—$OR^{14}$, —(C=O)$_r$—$NR^{14}R^{15}$, —C(=S)—$NR^{14}R^{15}$, —$NR^{14}$—(C=O)—$OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, with the proviso that not more than two of the $G^1$, $G^2$, $G^3$ and $G^4$ groups represent nitrogen, and with the proviso that at least one of the $G^1$, $G^2$, $G^3$ and $G^4$ groups represents CH, U represents C=O, C=S or $SO_2$, V represents O or $NR^{24}$, in which $R^{24}$ represents hydrogen, trideuteromethyl, $(C_1-C_6)$-alkyl, $(C_2-C_6)$-alkenyl, $(C_3-C_7)$-cycloalkyl, azetidinyl, pyrrolidinyl, piperidinyl or benzyl, in which $(C_1-C_6)$-alkyl for its part may be substituted by 1 to 3 substituents independently of one another selected from the group consisting of fluorine, trifluoromethyl, cyclopropyl, cyclobutyl, hydroxy, methoxy, ethoxy, methylsulphonyl, ethylsulphonyl, azetidinyl, oxetanyl, pyrrolidinyl, piperidinyl and morpholinyl, in which azetidinyl, oxetanyl, pyrrolidinyl, piperidinyl and morpholinyl for their part may be substituted by 1 or 2 substituents independently of one another selected from the group consisting of fluorine, trifluoromethyl, 2,2-difluoroethyl, 2,2,2-trifluoroethyl, methyl and ethyl, in which azetidinyl, pyrrolidinyl and piperidinyl for their part may be substituted by 1 or 2 substituents independently of one another selected from the group consisting of fluorine, trifluoromethyl, methyl, ethyl, cyclopropyl and cyclobutyl,
in which methyl and ethyl for their part may be substituted by 1 or 2 substituents independently of one another selected from the group consisting of fluorine, trifluoromethyl, cyclopropyl, cyclobutyl, hydroxy, methoxy and ethoxy,
and
in which benzyl may itself be substituted by 1 or 2 fluorine, chlorine, trifluoromethyl, methyl, ethyl, methylsulphonyl and ethylsulphonyl substituents,
W represents N or $CR^{25}$,
in which
$R^{25}$ represents hydrogen or oxo,
$R^{23}$ represents hydrogen, trideuteromethyl, $(C_1-C_6)$-alkyl or $(C_2-C_6)$-alkenyl,
in which $(C_1-C_4)$-alkyl may be substituted by 1 or 2 substituents independently of one another selected from the group consisting of fluorine, trifluoromethyl, cyclopropyl, cyclobutyl, hydroxy, methoxy and ethoxy,
$R^{25}$ represents hydrogen or oxo,
$R^{27}$ represents hydrogen, $(C_1-C_3)$-alkoxycarbonyl or aminosulphonyl,
in which $(C_1-C_3)$-alkoxycarbonyl may be substituted by 1 or 2 substituents independently of one another selected from the group consisting of fluorine, trifluoromethyl, hydroxy, methoxy and ethoxy,
$R^{28}$ represents hydrogen, trifluoromethyl, $(C_1-C_4)$-alkyl, $(C_3-C_6)$-cycloalkyl and phenyl,
in which phenyl may be substituted by 1 or 2 substituents independently of one another selected from the group consisting of fluorine, chlorine, trifluoromethyl, $(C_1-C_4)$-alkyl, methoxy and ethoxy,
$R^{29}$ represents hydrogen, trifluoromethyl, $(C_1-C_4)$-alkyl, cyclopropyl, cyclobutyl and phenyl,
in which phenyl may be substituted by 1 or 2 substituents independently of one another selected from the group consisting of fluorine, chlorine, trifluoromethyl, methyl, ethyl, methoxy and ethoxy,
$R^{30}$ represents hydrogen or $(C_1-C_6)$-alkyl,
in which $(C_1-C_6)$-alkyl may be substituted by 1 or 2 substituents independently of one another selected from the group consisting of fluorine, trifluoromethyl, cyclopropyl, cyclobutyl, hydroxy, methoxy and ethoxy,
$R^{31}$ represents hydrogen or $(C_1-C_6)$-alkyl,
in which $(C_1-C_6)$-alkyl may be substituted by 1 or 2 substituents independently of one another selected from the group consisting of fluorine, trifluoromethyl, cyclopropyl, cyclobutyl, hydroxy, methoxy and ethoxy,
and their salts, solvates and solvates of the salts.

Particular preference is given in the context of the present invention to compounds of the formula (I) in which
the ring Q represents a group of the formula (a-1-1)

(b-1-1)

(c-1-1)

(c-1-2)

(d-1)

(l-1-1)

where
* represents the point of attachment to —$CH_2$—$R^2$,
** represents the point of attachment to $R^3$,
$R^{1A}$ represents hydrogen or methyl,
$R^{1B}$ represents hydrogen or fluorine,
$R^{1C}$ represents hydrogen or chlorine,
$A^1$ represents N or CH,
$R^2$ represents 3,3,3-trifluoroprop-1-yl, 2,2,3,3-tetrafluoroprop-1-yl, 2,2,3,3,3-pentafluoroprop-1-yl, phenyl or pyridyl,
where phenyl is substituted by 1 to 3 fluorine substituents, and
where pyridyl may be substituted by 1 fluorine substituent,
$R^3$ represents a group of the formula where
## represents the point of attachment to the ring Q,
L represents N,
M represents $CR^4$, in which
R⁴ represents —R⁵, —OR⁶ or —NR⁷R⁸,
  in which
    R⁵ represents hydrogen or $(C_1-C_4)$-alkyl,
      in which $(C_1-C_4)$-alkyl for its part may be substituted by 1 or 2 substituents independently of one another selected from the group consisting of fluorine, difluoromethyl, trifluoromethyl, cyclopropyl, cyclobutyl, —(C=O)$_p$—OR⁹ and —C(=O)$_p$—NR⁹R¹⁰,
      in which
        p represents the number 0,
        R⁹ and R¹⁰ independently of one another each represent hydrogen, methyl, ethyl, trifluoromethyl, 2,2,2-trifluoroethyl, 1,1,2,2,2-pentafluoroethyl, cyclopropyl or cyclobutyl,
    R⁶ represents $(C_1-C_6)$-alkyl or pyrazolyl,
      in which $(C_1-C_6)$-alkyl may be substituted by 1 to 3 substituents independently of one another selected from the group consisting of fluorine, trifluoromethyl, —(C=O)$_p$—OR⁹ and —C(=O)$_p$—NR⁹R¹⁰,
      in which
        p represents the number 0 or 1,
        R⁹ and R¹⁰ independently of one another each represent hydrogen or methyl,
        or
        R⁹ and R¹⁰ together with the atom(s) to which they are respectively attached form an azetidinyl, pyrrolidinyl, piperidinyl, piperazinyl or morpholinyl ring,
          in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
      and
      in which pyrazolyl may be substituted by 1 or 2 substituents independently of one another selected from the group consisting of fluorine, difluoromethyl, trifluoromethyl, 2,2,2-trifluoroethyl, 1,1,2,2,2-pentafluoroethyl, methyl, cyclopropyl, cyclobutyl and cyclopentyl,
    R⁷ represents hydrogen, methyl or ethyl,
    R⁸ represents hydrogen, $(C_1-C_6)$-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
      in which $(C_1-C_6)$-alkyl may be substituted by 1 to 3 substituents independently of one another selected from the group consisting of fluorine, difluoromethyl, trifluoromethyl, cyclopropyl, cyclobutyl, cyclopentyl, trifluoromethoxy, —(C=O)$_p$—OR⁹, —(C=O)$_p$—NR⁹R¹⁰, tetrahydrofuranyl, pyrrolidinyl, tetrahydropyranyl, phenyl, furanyl, pyrazolyl, imidazolyl, triazolyl and pyridyl,
      in which
        p represents the number 0 or 1,
        R⁹ and R¹⁰ independently of one another each represent hydrogen, methyl, ethyl, trifluoromethyl, 2,2,2-trifluoroethyl, 1,1,2,2,2-pentafluoroethyl, cyclopropyl or cyclobutyl,
      and
      in which tetrahydrofuranyl, pyrrolidinyl, tetrahydropyranyl, phenyl, furanyl, pyrazolyl, imidazolyl, triazolyl and pyridyl for their part may be substituted by 1 or 2 substituents independently of one another selected from the group consisting of fluorine, chlorine, cyano, difluoromethyl, trifluoromethyl, methyl, ethyl, oxo, difluoromethoxy, trifluoromethoxy, methoxy and ethoxy,
      and
      in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl and trifluoromethoxy,
E¹ represents NR¹⁸,
  in which
    R¹⁸ represents hydrogen,
E² represents N,
E³ represents N or CR¹⁹,
  in which
    R¹⁹ represents hydrogen, fluorine, difluoromethyl, trifluoromethyl, $(C_1-C_4)$-alkyl or a group of the formula -M-R¹³,
      in which $(C_1-C_4)$-alkyl may be substituted by 1 to 3 substituents independently of one another selected from the group consisting of fluorine, trifluoromethyl, cyclopropyl and cyclobutyl,
      and in which
        M represents a bond, methylene, ethane-1,2-diyl or propane-1,3-diyl,
        R¹³ represents —(C=O)$_r$—OR¹⁴, —(C=O)$_r$—NR¹⁴R¹⁵, phenyl, thiazolyl, triazolyl, oxadiazolyl, thiadiazolyl or pyrimidinyl,
          in which
            r represents the number 0 or 1,
            R¹⁴ and R¹⁵ independently of one another each represent hydrogen, methyl, ethyl, cyclopropyl, cyclobutyl or phenyl,
              in which methyl and ethyl may additionally be substituted by 1 or 2 substituents independently of one another selected from the group consisting of fluorine, difluoromethyl, trifluoromethyl, cyclopropyl, cyclobutyl, hydroxy, trifluoromethoxy and methoxy,
              and
              in which phenyl, thiazolyl, triazolyl, oxadiazolyl, thiadiazolyl and pyrimidinyl may each in turn be substituted by 1 or 2 substituents selected independently of one another from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
U represents C(=O),
V represents NR²⁴,
  in which
    R²⁴ represents trideuteromethyl, $(C_1-C_6)$-alkyl, cyclopropyl, cyclobutyl, azetidin-3-yl, pyrrolidin-3-yl or piperidin-4-yl, in which $(C_1-C_6)$-alkyl for its part may be substituted by 1 to 3 substituents independently of one another selected from the group consisting of fluorine, trifluoromethyl, cyclopropyl, cyclobutyl, hydroxy, oxetanyl and morpholin-4-yl, and in which azetidin-3-yl, pyrrolidin-3-yl and piperidin-4-yl for their part may be substituted by 1 or 2 substituents independently of one another selected from the group consisting of fluorine, trifluoromethyl, 2,2-difluoroethyl, 2,2,2-trifluoroethyl, cyclopropyl and cyclobutyl, $R^{23}$ represents hydrogen, and their salts, solvates and solvates of the salts.

Preference is given in the context of the present invention to compounds of the formula (I) in which the ring Q represents a group of the formula

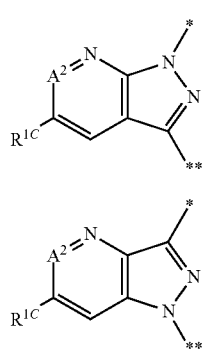

(a-1-2)

(b-1-2)

where

* represents the point of attachment to —$CH_2$—$R^2$,

** represents the point of attachment to $R^3$, $R^{1C}$ represents hydrogen or fluorine, $A^2$ represents N or CH, $R^2$ represents cyclopropyl, cyclobutyl, cyclopentyl, cyclohexyl, pyridyl, pyrimidinyl, pyrazinyl or pyridazinyl, where cyclopropyl, cyclobutyl, cyclopentyl, cyclohexyl, pyridyl, pyrimidinyl, pyrazinyl and pyridazinyl may be substituted by 1 or 2 fluorine substituents, $R^3$ represents a group of the formula

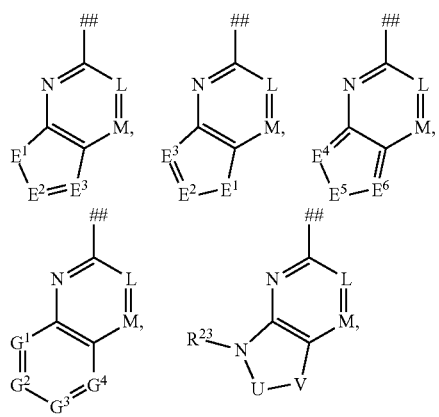

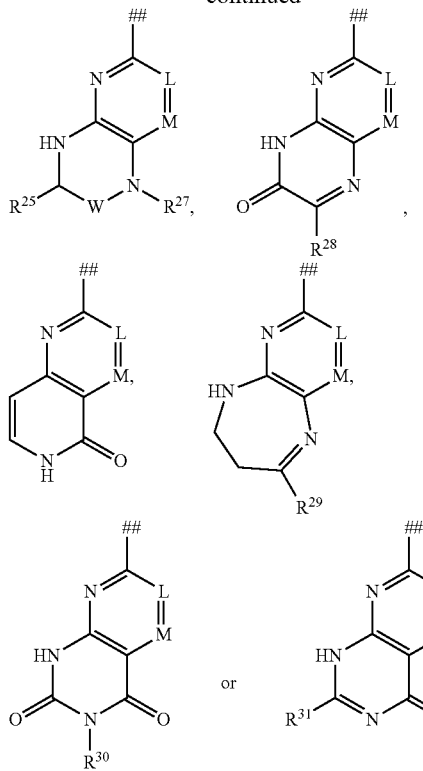

where ## represents the point of attachment to the ring Q,

L represents CH or N,

M represents $CR^4$ or N, in which $R^4$ represents —$R^5$, —$OR^6$ or —$NR^7R^8$, in which $R^5$ represents hydrogen, chlorine, cyano, $(C_1-C_4)$-alkyl or $(C_2-C_4)$-alkynyl, in which $(C_1-C_4)$-alkyl and $(C_2-C_4)$-alkynyl for their part may be substituted by 1 or 2 substituents independently of one another selected from the group consisting of fluorine, difluoromethyl, trifluoromethyl, cyclopropyl, cyclobutyl, cyclopentyl, difluoromethoxy, trifluoromethoxy, —(C=O)$_p$—$OR^9$ and —C(=O)$_p$—$NR^9R^{10}$, in which p represents the number 0, $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino, $R^6$ represents $(C_1-C_6)$-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl may be substituted by 1 to 3 substituents independently of one another selected from the group consisting of fluorine, difluoromethyl, trifluoromethyl, cyclopropyl, cyclobutyl, cyclopentyl, difluoromethoxy, trifluoromethoxy, $—(C=O)_p—OR^9$, $—(C=O)_p—NR^9R^{10}$ and $—NR^9—(C=O)—R^{10}$, and in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl may be substituted by 1 to 3 substituents independently of one another selected from the group consisting of fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, $—(C=O)_p—OR^9$ and $—(C=O)_p—NR^9R^{10}$, in which p represents the number 0 or 1, $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino, $R^7$ represents hydrogen, methyl or ethyl, $R^8$ represents hydrogen, $(C_1-C_6)$-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl, in which $(C_1-C_6)$-alkyl, cyclopropyl, cyclobutyl and cyclopentyl are substituted by 1 to 3 substituents independently of one another selected from the group consisting of fluorine, difluoromethyl, trifluoromethyl methyl, ethyl, cyclopropyl, cyclobutyl, cyclopentyl, difluoromethoxy, trifluoromethoxy, $—(C=O)_p—OR^9$, $—(C=O)_p—NR^9R^{10}$, $—NR^9—(C=O)—R^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl, in which p represents the number 0 or 1, $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino and in which oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part may be substituted by 1 or 2 substituents independently of one another selected from the group consisting of fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy, and in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl, cyclopropyl, cyclobutyl, cyclopentyl, difluoromethoxy, trifluoromethoxy, oxo, $—(C=O)_p—OR^9$ and $—(C=O)_p—NR^9R^{10}$, in which p represents the number 0 or 1, $R^9$ and $R^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl, or $R^9$ and $R^{10}$ together with the atom(s) to which they are respectively attached form an azetidinyl, pyrrolidinyl, piperidinyl, piperazinyl or morpholinyl ring, in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino, or R$^7$ and R$^8$ together with the nitrogen atom to which they are attached form an azetidinyl, pyrrolidinyl, imidazolidinyl, piperidinyl, dihydropiperidinyl, piperazinyl, morpholinyl, pyrazolyl, imidazolyl or triazolyl ring,
  in which the azetidinyl, pyrrolidinyl, imidazolidinyl, piperidinyl, dihydropiperidinyl, piperazinyl, morpholinyl, pyrazolyl, imidazolyl or triazolyl ring may be substituted by 1 or 2 substituents independently of one another selected from the group consisting of fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, E$^1$ represents O, S or NR$^{18}$,
  in which
  R$^{18}$ represents hydrogen, trifluoromethyl or (C$_1$-C$_4$)-alkyl,
    in which (C$_1$-C$_4$)-alkyl for its part may be substituted by 1 or 2 substituents independently of one another selected from the group consisting of fluorine, trifluoromethyl, hydroxy, methoxy and ethoxy, E$^2$ represents N, E$^3$ represents N or CR$^{19}$,
  in which
  R$^{19}$ represents hydrogen, fluorine, difluoromethyl, trifluoromethyl, (C$_1$-C$_4$)-alkyl, cyclopropyl, cyclobutyl, cyclopentyl or a group of the formula -M-R$^{13}$,
    in which (C$_1$-C$_4$)-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy,
    and in which
    M represents a bond, methylene, ethane-1,2-diyl or propane-1,3-diyl,
    R$^{13}$ represents —(C=O)$_r$—OR$^{14}$, —(C=O)$_r$—NR$^{14}$R$^{15}$, —C(=S)—NR$^{14}$R$^{15}$, —NR$^{14}$—(C=O)—OR$^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
      in which
      r represents the number 0 or 1,
      R$^{14}$ and R$^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
        in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
      R$^{17}$ represents methyl, ethyl, isopropyl, cyclopropyl, cyclobutyl, cyclopentyl,
      and
      in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, E$^4$ and E$^6$ independently of one another each represent N or CR$^{20}$,
  in which
  R$^{20}$ represents hydrogen, fluorine, difluoromethyl, trifluoromethyl, (C$_1$-C$_4$)-alkyl, cyclopropyl, cyclobutyl, cyclopentyl or a group of the formula -M-R$^{13}$,
    in which (C$_1$-C$_4$)-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy,
    and in which
    M represents a bond, methylene, ethane-1,2-diyl or propane-1,3-diyl,
    R$^{13}$ represents —(C=O)$_r$—OR$^{14}$, —(C=O)$_r$—NR$^{14}$R$^{15}$, —C(=S)—NR$^{14}$R$^{15}$, —NR$^{14}$—(C=O)—OR$^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
      in which
      r represents the number 0 or 1,
      R$^{14}$ and R$^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
        in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
      R$^{17}$ represents methyl, ethyl, isopropyl, cyclopropyl, cyclobutyl, cyclopentyl,
      and
      in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, E$^5$ represents NR$^{21}$,
  in which
  R$^{21}$ represents hydrogen or (C$_1$-C$_4$)-alkyl,
    in which (C$_1$-C$_4$)-alkyl may itself be substituted by 1 or 2 substituents each independently of one another selected from the group consisting of fluorine, trifluoromethyl, hydroxy, methoxy and ethoxy, $G^1$, $G^2$, $G^3$ and $G^4$ independently of one another each represent N or $CR^{22}$,
in which
$R^{22}$ represents hydrogen, fluorine, difluoromethyl, trifluoromethyl, ($C_1$-$C_4$)-alkyl, cyclopropyl, cyclobutyl, cyclopentyl or a group of the formula -M-$R^{13}$,
in which ($C_1$-$C_4$)-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy,
and in which
M represents a bond, methylene, ethane-1,2-diyl or propane-1,3-diyl,
$R^{13}$ represents —(C=O)$_r$—$OR^{14}$, —(C=O)$_r$—$NR^{14}R^{15}$, —C(=S)—$NR^{14}R^{15}$, —$NR^{14}$—(C=O)—$OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl,
in which
r represents the number 0 or 1,
$R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl,
in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino,
$R^{17}$ represents methyl, ethyl, isopropyl, cyclopropyl, cyclobutyl, cyclopentyl,
and
in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy,
with the proviso that not more than two of the $G^1$, $G^2$, $G^3$ and $G^4$ groups represent nitrogen,
and
with the proviso that at least one of the $G^1$, $G^2$, $G^3$ and $G^4$ groups represents CH,
U represents C=O, C=S or $SO_2$,
V represents O or $NR^{24}$,
in which
$R^{24}$ represents hydrogen, trideuteromethyl, ($C_1$-$C_6$)-alkyl, ($C_2$-$C_6$)-alkenyl, ($C_3$-$C_7$)-cycloalkyl, azetidinyl, pyrrolidinyl, piperidinyl or benzyl,
in which ($C_1$-$C_6$)-alkyl for its part may be substituted by 1 to 3 substituents independently of one another selected from the group consisting of fluorine, trifluoromethyl, cyclopropyl, cyclobutyl, hydroxy, methoxy, ethoxy, methylsulphonyl, ethylsulphonyl, azetidinyl, oxetanyl, pyrrolidinyl, piperidinyl and morpholinyl,
in which azetidinyl, oxetanyl, pyrrolidinyl, piperidinyl and morpholinyl for their part may be substituted by 1 or 2 substituents independently of one another selected from the group consisting of fluorine, trifluoromethyl, 2,2-difluoroethyl, 2,2,2-trifluoroethyl, methyl and ethyl,
in which azetidinyl, pyrrolidinyl and piperidinyl for their part may be substituted by 1 or 2 substituents independently of one another selected from the group consisting of fluorine, trifluoromethyl, methyl, ethyl, cyclopropyl and cyclobutyl,
in which methyl and ethyl for their part may be substituted by 1 or 2 substituents independently of one another selected from the group consisting of fluorine, trifluoromethyl, cyclopropyl, cyclobutyl, hydroxy, methoxy and ethoxy,
and
in which benzyl may itself be substituted by 1 or 2 fluorine, chlorine, trifluoromethyl, methyl, ethyl, methylsulphonyl and ethylsulphonyl substituents,
W represents N or $CR^{25}$,
in which
$R^{25}$ represents hydrogen or oxo,
$R^{23}$ represents hydrogen, trideuteromethyl, ($C_1$-$C_6$)-alkyl or ($C_2$-$C_6$)-alkenyl,
in which ($C_1$-$C_4$)-alkyl may be substituted by 1 or 2 substituents independently of one another selected from the group consisting of fluorine, trifluoromethyl, cyclopropyl, cyclobutyl, hydroxy, methoxy and ethoxy,
$R^{25}$ represents hydrogen or oxo,
$R^{27}$ represents hydrogen, ($C_1$-$C_3$)-alkoxycarbonyl or aminosulphonyl,
in which ($C_1$-$C_3$)-alkoxycarbonyl may be substituted by 1 or 2 substituents independently of one another selected from the group consisting of fluorine, trifluoromethyl, hydroxy, methoxy and ethoxy,
$R^{28}$ represents hydrogen, trifluoromethyl, ($C_1$-$C_4$)-alkyl, ($C_3$-$C_6$)-cycloalkyl and phenyl,
in which phenyl may be substituted by 1 or 2 substituents independently of one another selected from the group consisting of fluorine, chlorine, trifluoromethyl, ($C_1$-$C_4$)-alkyl, methoxy and ethoxy,
$R^{29}$ represents hydrogen, trifluoromethyl, ($C_1$-$C_4$)-alkyl, cyclopropyl, cyclobutyl and phenyl,
in which phenyl may be substituted by 1 or 2 substituents independently of one another selected from the group consisting of fluorine, chlorine, trifluoromethyl, methyl, ethyl, methoxy and ethoxy,
$R^{30}$ represents hydrogen or ($C_1$-$C_6$)-alkyl,
in which ($C_1$-$C_6$)-alkyl may be substituted by 1 or 2 substituents independently of one another selected from the group consisting of fluorine, trifluoromethyl, cyclopropyl, cyclobutyl, hydroxy, methoxy and ethoxy,
$R^{31}$ represents hydrogen or ($C_1$-$C_6$)-alkyl,
in which ($C_1$-$C_6$)-alkyl may be substituted by 1 or 2 substituents independently of one another selected from the group consisting of fluorine, trifluoromethyl, cyclopropyl, cyclobutyl, hydroxy, methoxy and ethoxy,
and their salts, solvates and solvates of the salts.

Preference is given in the context of the present invention to compounds of the formula (I) in which the ring Q represents a group of the formula

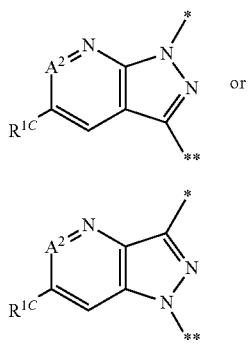

(a-1-2)

or (b-1-2)

where
* represents the point of attachment to —CH$_2$—R$^2$,
** represents the point of attachment to R$^3$,
R$^{1C}$ represents hydrogen or fluorine,
A$^2$ represents N or CH,
R$^2$ represents trifluoromethyl, 2,2,2-trifluoroethyl, 3,3,3-trifluoroprop-1-yl, 2,2,3,3-tetrafluorprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
where phenyl is substituted by 1 to 3 fluorine substituents, and
where cyclopropyl, cyclobutyl, cyclopentyl, cyclohexyl, pyridyl, pyrimidinyl, pyrazinyl and pyridazinyl may be substituted by 1 or 2 fluorine substituents,
R$^3$ represents a group of the formula

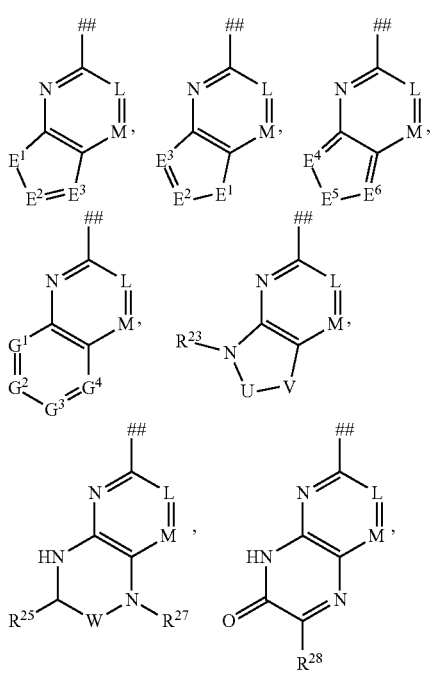

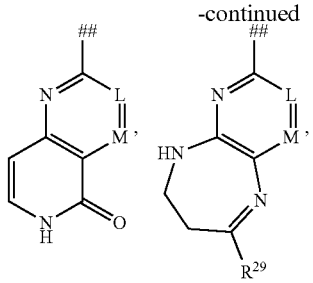

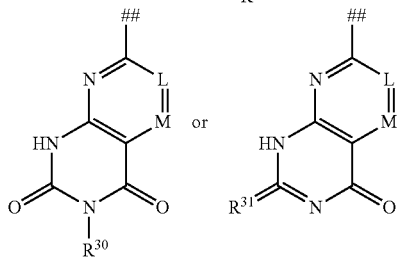

where
## represents the point of attachment to the ring Q,
L represents CH or N,
M represents CR$^4$ or N,
in which
R$^4$ represents —R$^5$, —OR$^6$ or —NR$^7$R$^8$,
in which
R$^5$ represents trifluoromethyl or (C$_1$-C$_4$)-alkyl,
in which (C$_1$-C$_4$)-alkyl for its part may be substituted by 1 or 2 substituents independently of one another selected from the group consisting of difluoromethyl, trifluoromethyl, cyclopropyl, cyclobutyl, cyclopentyl, difluoromethoxy, trifluoromethoxy, —(C═O)$_p$—OR$^9$ and —C(═O)$_p$—NR$^9$R$^{10}$,
in which
p represents the number 0,
R$^9$ and R$^{10}$ independently of one another each represent methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ together with the atom(s) to which they are respectively attached form an azetidinyl, pyrrolidinyl, piperidinyl, piperazinyl or morpholinyl ring,
in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
R$^6$ represents (C$_1$-C$_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C$_1$-C$_6$)-alkyl may be substituted by 1 to 3 substituents independently of one another selected from the group consisting of difluoromethyl, trifluoromethyl, cyclopropyl, cyclobutyl, cyclopentyl, difluoromethoxy, trifluoromethoxy, ($C_1$-$C_4$)-alkoxy, —(C=O)—OR$^9$, —(C=O)—NR$^9$R$^{10}$ and —NR$^9$—(C=O)—R$^{10}$,
in which
R$^9$ and R$^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ together with the atom(s) to which they are respectively attached form an azetidinyl, pyrrolidinyl, piperidinyl, piperazinyl or morpholinyl ring,
in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
and
in which cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl may be substituted by 1 to 3 substituents independently of one another selected from the group consisting of fluorine, difluoromethyl, trifluoromethyl, 2,2,2-trifluoroethyl, 1,1,2,2,2-pentafluoroethyl, methyl, ethyl, isopropyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
in which in each case
p represents the number 0 or 1,
R$^9$ and R$^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ together with the atom(s) to which they are respectively attached form an azetidinyl, pyrrolidinyl, piperidinyl, piperazinyl or morpholinyl ring,
in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
R$^7$ represents hydrogen, methyl or ethyl,
R$^8$ represents ($C_1$-$C_6$)-alkyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which ($C_1$-$C_6$)-alkyl, cyclopropyl, cyclobutyl and cyclopentyl are substituted by 1 to 3 substituents independently of one another selected from the group consisting of fluorine, difluoromethyl, trifluoromethyl methyl, ethyl, cyclopropyl, cyclobutyl, cyclopentyl, difluoromethoxy, trifluoromethoxy, ($C_1$-$C_4$)-alkoxy, —(C=O)—OR$^9$, —(C=O)—NR$^9$R$^{10}$, —NR$^9$—(C=O)—R$^{10}$, oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl,
in which
R$^9$ and R$^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ together with the atom(s) to which they are respectively attached form an azetidinyl, pyrrolidinyl, piperidinyl, piperazinyl or morpholinyl ring,
in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino
and
in which oxetanyl, azetidinyl, tetrahydrofuranyl, pyrrolidinyl, tetrahydropyranyl, piperidinyl, piperazinyl, morpholinyl, phenyl, furanyl, pyrazolyl, imidazolyl, oxazolyl, thiazolyl, triazolyl, oxadiazolyl, thiadiazolyl, pyridyl and pyrimidinyl for their part may be substituted by 1 or 2 substituents independently of one another selected from the group consisting of fluorine, chlorine, cyano, difluoromethyl, trifluoromethyl, methyl, ethyl, cyclopropyl, cyclobutyl, cyclopentyl, hydroxy, oxo, difluoromethoxy, trifluoromethoxy, methoxy and ethoxy,
and
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl, cyclopropyl, cyclobutyl, cyclopentyl, difluoromethoxy, trifluoromethoxy, oxo, —(C=O)$_p$—OR$^9$ and —(C=O)$_p$—NR$^9$R$^{10}$,
in which
p represents the number 0 or 1,
R$^9$ and R$^{10}$ independently of one another each represent hydrogen, methyl, ethyl, isopropyl, trifluoromethyl, 2,2,2-trifluoroethyl, 1,1,2,2,2-pentafluoroethyl, cyclopropyl, cyclobutyl or cyclopentyl,
or
R$^9$ and R$^{10}$ together with the atom(s) to which they are respectively attached form an azetidinyl, pyrrolidinyl, piperidinyl, piperazinyl or morpholinyl ring,
in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino, or $R^7$ and $R^8$ together with the nitrogen atom to which they are attached form an azetidinyl, pyrrolidinyl, imidazolidinyl, piperidinyl, dihydropiperidinyl, piperazinyl, morpholinyl, pyrazolyl, imidazolyl or triazolyl ring, in which the azetidinyl, pyrrolidinyl, imidazolidinyl, piperidinyl, dihydropiperidinyl, piperazinyl, morpholinyl, pyrazolyl, imidazolyl independently of one another selected from the group consisting of fluorine, cyano, difluoromethyl, trifluoromethyl, 2,2,2-trifluoroethyl, 1,1,2,2,2-pentafluoroethyl, methyl, ethyl, 1-hydroxyethyl, cyclopropyl, cyclobutyl, cyclopentyl, hydroxy, oxo, methoxy, ethoxy, difluoromethoxy and trifluoromethoxy, $E^1$ represents O, S or $NR^{18}$, in which $R^{18}$ represents hydrogen, trifluoromethyl or $(C_1-C_4)$-alkyl, in which $(C_1-C_4)$-alkyl for its part may be substituted by 1 or 2 substituents independently of one another selected from the group consisting of fluorine, trifluoromethyl, hydroxy, methoxy and ethoxy, $E^2$ represents N, $E^3$ represents N or $CR^{19}$, in which $R^{19}$ represents hydrogen, fluorine, difluoromethyl, trifluoromethyl, $(C_1-C_4)$-alkyl, cyclopropyl, cyclobutyl, cyclopentyl or a group of the formula $-M-R^{13}$, in which $(C_1-C_4)$-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents $-(C=O)_r-OR^{14}$, $-(C=O)_r-NR^{14}R^{15}$, $-C(=S)-NR^{14}R^{15}$, $-NR^{14}-(C=O)-OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, $E^4$ and $E^6$ independently of one another each represent N or $CR^{20}$, in which $R^{20}$ represents hydrogen, fluorine, difluoromethyl, trifluoromethyl, $(C_1-C_4)$-alkyl, cyclopropyl, cyclobutyl, cyclopentyl or a group of the formula $-M-R^{13}$, in which $(C_1-C_4)$-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents $-(C=O)_r-OR^{14}$, $-(C=O)_r-NR^{14}R^{15}$, $-C(=S)-NR^{14}R^{15}$, $-NR^{14}-(C=O)-OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, $E^5$ represents $NR^{21}$, in which $R^{21}$ represents hydrogen or $(C_1-C_4)$-alkyl, in which $(C_1-C_4)$-alkyl may itself be substituted by 1 or 2 substituents each independently of one another selected from the group consisting of fluorine, trifluoromethyl, hydroxy, methoxy and ethoxy, $G^1$, $G^2$, $G^3$ and $G^4$ independently of one another each represent N or $CR^{22}$, in which $R^{22}$ represents hydrogen, fluorine, difluoromethyl, trifluoromethyl, $(C_1-C_4)$-alkyl, cyclopropyl, cyclobutyl, cyclopentyl or a group of the formula -M-$R^{13}$, in which $(C_1-C_4)$-alkyl may be substituted by 1 to 3 substituents selected independently of one another from the group consisting of fluorine, cyano, trifluoromethyl, cyclopropyl, cyclobutyl, cyclopentyl, difluoromethoxy and trifluoromethoxy, and in which M represents a bond, methylene, ethane-1,2-diyl or propane-1,3-diyl, $R^{13}$ represents —(C=O)$_r$—$OR^{14}$, —(C=O)$_r$—$NR^{14}R^{15}$, —C(=S)—$NR^{14}R^{15}$, —$NR^{14}$—(C=O)—$OR^{17}$, oxadiazolonyl, oxadiazolethionyl, phenyl, oxazolyl, thiazolyl, pyrazolyl, triazolyl, oxadiazolyl, thiadiazolyl, pyridyl, pyrimidinyl or pyrazinyl, in which r represents the number 0 or 1, $R^{14}$ and $R^{15}$ independently of one another each represent hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents independently of one another selected from the group consisting of fluorine, difluoromethyl, trifluoromethyl, cyclopropyl, cyclobutyl, cyclopentyl, hydroxy, difluoromethoxy, trifluoromethoxy, methoxy, ethoxy, hydroxycarbonyl, methoxycarbonyl, ethoxycarbonyl and amino, $R^{17}$ represents methyl, ethyl, isopropyl, cyclopropyl, cyclobutyl, cyclopentyl, and in which oxadiazolonyl, oxadiazolethionyl, phenyl, oxazolyl, thiazolyl, pyrazolyl, triazolyl, oxadiazolyl, thiadiazolyl, pyridyl, pyrimidinyl and pyrazinyl for their part may be substituted by 1 or 2 substituents independently of one another selected from the group consisting of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxy, methoxy and ethoxy, with the proviso that not more than two of the $G^1$, $G^2$, $G^3$ and $G^4$ groups represent nitrogen, and with the proviso that at least one of the $G^1$, $G^2$, $G^3$ and $G^4$ groups represents CH, U represents C=O, C=S or $SO_2$, V represents O or $NR^{24}$, in which $R^{24}$ represents hydrogen, trideuteromethyl, $(C_1-C_6)$-alkyl, $(C_2-C_6)$-alkenyl, $(C_3-C_7)$-cycloalkyl, azetidinyl, pyrrolidinyl, piperidinyl or benzyl, in which $(C_1-C_6)$-alkyl for its part may be substituted by 1 to 3 substituents independently of one another selected from the group consisting of fluorine, trifluoromethyl, cyclopropyl, cyclobutyl, hydroxy, methoxy, ethoxy, methylsulphonyl, ethylsulphonyl, azetidinyl, oxetanyl, pyrrolidinyl, piperidinyl and morpholinyl, in which azetidinyl, oxetanyl, pyrrolidinyl, piperidinyl and morpholinyl for their part may be substituted by 1 or 2 substituents independently of one another selected from the group consisting of fluorine, trifluoromethyl, 2,2-difluoroethyl, 2,2,2-trifluoroethyl, methyl and ethyl, in which azetidinyl, pyrrolidinyl and piperidinyl for their part may be substituted by 1 or 2 substituents independently of one another selected from the group consisting of fluorine, trifluoromethyl, methyl, ethyl, cyclopropyl and cyclobutyl, in which methyl and ethyl for their part may be substituted by 1 or 2 substituents independently of one another selected from the group consisting of fluorine, trifluoromethyl, cyclopropyl, cyclobutyl, hydroxy, methoxy and ethoxy, and in which benzyl may itself be substituted by 1 or 2 fluorine, chlorine, trifluoromethyl, methyl, ethyl, methylsulphonyl and ethylsulphonyl substituents, W represents N or $CR^{25}$, in which $R^{25}$ represents hydrogen or oxo, $R^{23}$ represents hydrogen, trideuteromethyl, $(C_1-C_6)$-alkyl or $(C_2-C_6)$-alkenyl, in which $(C_1-C_4)$-alkyl may be substituted by 1 or 2 substituents independently of one another selected from the group consisting of fluorine, trifluoromethyl, cyclopropyl, cyclobutyl, hydroxy, methoxy and ethoxy, $R^{25}$ represents hydrogen or oxo, $R^{27}$ represents hydrogen, $(C_1-C_3)$-alkoxycarbonyl or aminosulphonyl, in which $(C_1-C_3)$-alkoxycarbonyl may be substituted by 1 or 2 substituents independently of one another selected from the group consisting of fluorine, trifluoromethyl, hydroxy, methoxy and ethoxy, $R^{28}$ represents hydrogen, trifluoromethyl, $(C_1-C_4)$-alkyl, $(C_3-C_6)$-cycloalkyl and phenyl, in which phenyl may be substituted by 1 or 2 substituents independently of one another selected from the group consisting of fluorine, chlorine, trifluoromethyl, $(C_1-C_4)$-alkyl, methoxy and ethoxy, $R^{29}$ represents hydrogen, trifluoromethyl, $(C_1-C_4)$-alkyl, cyclopropyl, cyclobutyl and phenyl, in which phenyl may be substituted by 1 or 2 substituents independently of one another selected from the group consisting of fluorine, chlorine, trifluoromethyl, methyl, ethyl, methoxy and ethoxy, $R^{30}$ represents hydrogen or $(C_1-C_6)$-alkyl, in which $(C_1-C_6)$-alkyl may be substituted by 1 or 2 substituents independently of one another selected from the group consisting of fluorine, trifluoromethyl, cyclopropyl, cyclobutyl, hydroxy, methoxy and ethoxy, $R^{31}$ represents hydrogen or $(C_1-C_6)$-alkyl, in which $(C_1-C_6)$-alkyl may be substituted by 1 or 2 substituents independently of one another selected from the group consisting of fluorine, trifluoromethyl, cyclopropyl, cyclobutyl, hydroxy, methoxy and ethoxy, and their salts, solvates and solvates of the salts, except for the compounds:
2-[1-(2-fluorobenzyl)-1H-pyrazolo[3,4-b]pyridin-3-yl]-8-methyl-9H-purine,
2-[1-(2-fluorobenzyl)-1H-pyrazolo[3,4-b]pyridin-3-yl]-8-methyl-9H-purine-6-amine,
N-butyl-2-[1-(2-fluorobenzyl)-1H-pyrazolo[3,4-b]pyridin-3-yl]-8-methyl-9H-purine-6-amine.

Preference is given in the context of the present invention to compounds of the formula (I) in which
the ring Q represents a group of the formula

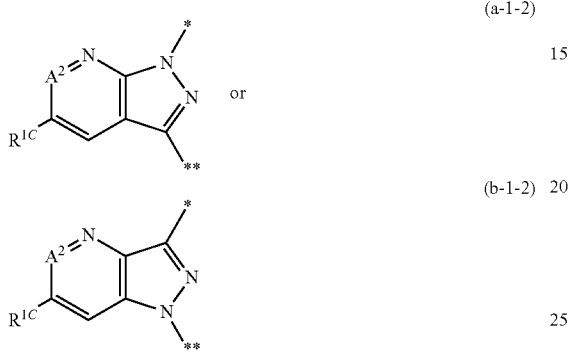

where
* represents the point of attachment to —CH$_2$—R$^2$,
** represents the point of attachment to R$^3$,
R$^{1C}$ represents hydrogen or fluorine,
A$^2$ represents CH,
R$^2$ represents pyridyl or pyrimidinyl,
  where pyridyl and pyrimidinyl may be substituted by 1 fluorine substituent,
R$^3$ represents a group of the formula

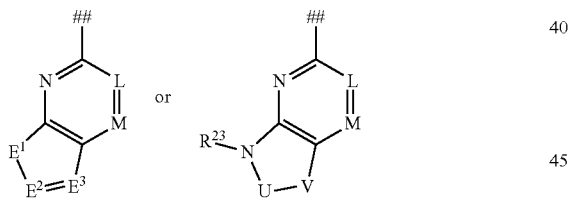

where
## represents the point of attachment to the ring Q,
L represents N,
M represents CR$^4$,
  in which
  R$^4$ represents —R$^5$, —OR$^6$ or —NR$^7$R$^8$,
    in which
    R$^5$ represents hydrogen, trifluoromethyl or (C$_1$-C$_4$)-alkyl,
      in which (C$_1$-C$_4$)-alkyl for its part may be substituted by 1 or 2 substituents independently of one another selected from the group consisting of fluorine, difluoromethyl, trifluoromethyl, cyclopropyl, cyclobutyl, —(C=O)$_p$—OR$^9$ and —C(=O)$_p$—NR$^9$R$^{10}$,
        in which
        p represents the number 0,
        R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
    R$^6$ represents (C$_1$-C$_6$)-alkyl or pyrazolyl,
      in which (C$_1$-C$_6$)-alkyl may be substituted by 1 to 3 substituents independently of one another selected from the group consisting of fluorine, trifluoromethyl, —(C=O)$_p$—OR$^9$ and —C(=O)$_p$—NR$^9$R$^{10}$,
        in which
        p represents the number 0 or 1,
        R$^9$ and R$^{10}$ independently of one another each represent hydrogen or methyl,
        or
        R$^9$ and R$^{10}$ together with the atom(s) to which they are respectively attached form an azetidinyl, pyrrolidinyl, piperidinyl, piperazinyl or morpholinyl ring,
          in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
      and
      in which pyrazolyl may be substituted by 1 or 2 substituents independently of one another selected from the group consisting of fluorine, difluoromethyl, trifluoromethyl, 2,2,2-trifluoroethyl, 1,1,2,2,2-pentafluoroethyl, methyl, cyclopropyl, cyclobutyl and cyclopentyl,
    R$^7$ represents hydrogen, methyl or ethyl,
    R$^8$ represents hydrogen, (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
      in which (C$_1$-C$_6$)-alkyl may be substituted by 1 to 3 substituents independently of one another selected from the group consisting of fluorine, difluoromethyl, trifluoromethyl, cyclopropyl, cyclobutyl, cyclopentyl, trifluoromethoxy, —(C=O)$_p$—OR$^9$, —(C=O)$_p$—NR$^9$R$^{10}$, tetrahydrofuranyl, pyrrolidinyl, tetrahydropyranyl, phenyl, furanyl, pyrazolyl, imidazolyl, triazolyl and pyridyl,
        in which
        p represents the number 0 or 1,
        R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
      and
      in which tetrahydrofuranyl, pyrrolidinyl, tetrahydropyranyl, phenyl, furanyl, pyrazolyl, imidazolyl, triazolyl and pyridyl for their part may be substituted by 1 or 2 substituents independently of one another selected from the group consisting of fluorine, chlorine, cyano, difluoromethyl, trifluoromethyl, methyl, ethyl, oxo, difluoromethoxy, trifluoromethoxy, methoxy and ethoxy,
      and
      in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl and trifluoromethoxy, $E^1$ represents $NR^{18}$,
in which
$R^{18}$ represents hydrogen,
$E^2$ represents N,
$E^3$ represents N or $CR^{19}$,
in which
$R^{19}$ represents hydrogen, fluorine, difluoromethyl, trifluoromethyl, ($C_1$-$C_4$)-alkyl or a group of the formula -M-$R^{13}$,
in which ($C_1$-$C_4$)-alkyl may be substituted by 1 to 3 substituents independently of one another selected from the group consisting of fluorine, trifluoromethyl, cyclopropyl and cyclobutyl,
and in which
M represents a bond, methylene, ethane-1,2-diyl or propane-1,3-diyl,
$R^{13}$ represents —(C=O)$_r$—$OR^{14}$, —(C=O)$_r$—$NR^{14}R^{15}$, phenyl, thiazolyl, triazolyl, oxadiazolyl, thiadiazolyl or pyrimidinyl,
in which
r represents the number 0 or 1,
$R^{14}$ and $R^{15}$ independently of one another each represent hydrogen, methyl, ethyl, cyclopropyl, cyclobutyl or phenyl,
in which methyl and ethyl may additionally be substituted by 1 to 2 substituents independently of one another selected from the group consisting of fluorine, difluoromethyl, trifluoromethyl, cyclopropyl, cyclobutyl, hydroxy, trifluoromethoxy and methoxy,
and
in which phenyl, thiazolyl, triazolyl, oxadiazolyl, thiadiazolyl and pyrimidinyl may each in turn be substituted by 1 or 2 substituents selected independently of one another from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
U represents C(=O),
V represents $NR^{24}$,
in which
$R^{24}$ represents trideuteromethyl, ($C_1$-$C_6$)-alkyl, cyclopropyl, cyclobutyl, azetidin-3-yl, pyrrolidin-3-yl or piperidin-4-yl,
in which ($C_1$-$C_6$)-alkyl for its part may be substituted by 1 to 3 substituents independently of one another selected from the group consisting of fluorine, trifluoromethyl, cyclopropyl, cyclobutyl, hydroxy, oxetanyl and morpholin-4-yl,
and
in which azetidin-3-yl, pyrrolidin-3-yl and piperidin-4-yl for their part may be substituted by 1 or 2 substituents independently of one another selected from the group consisting of fluorine, trifluoromethyl, 2,2-difluoroethyl, 2,2,2-trifluoroethyl, cyclopropyl and cyclobutyl,
$R^{23}$ represents hydrogen,
and their salts, solvates and solvates of the salts.

Preference is given in the context of the present invention to compounds of the formula (I) in which
the ring Q represents a group of the formula

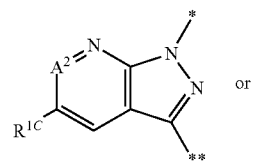

(a-1-2)

or

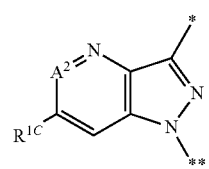

(b-1-2)

where
* represents the point of attachment to —$CH_2$—$R^2$,
** represents the point of attachment to $R^3$,
$R^{1C}$ represents hydrogen or fluorine,
$A^2$ represents CH,
$R^2$ represents 3-fluoropyrid-2-yl,
$R^3$ represents a group of the formula

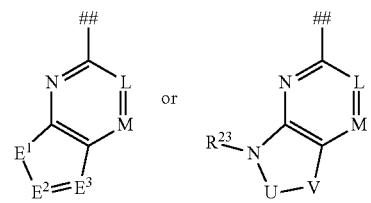

where
## represents the point of attachment to the ring Q,
L represents N,
M represents $CR^1$,
in which
$R^4$ represents —$R^5$ or —$NR^7R^8$,
in which
$R^5$ represents hydrogen,
$R^7$ represents hydrogen,
$R^8$ represents hydrogen or ($C_1$-$C_6$)-alkyl,
in which ($C_1$-$C_6$)-alkyl is substituted by 1 to 3 substituents independently of one another selected from the group consisting of fluorine, trifluoromethyl, cyclopropyl, cyclobutyl, —(C=O)$_p$—$OR^9$ and —C(=O)$_p$—$NR^9R^{10}$,
in which
p represents the number 0,
$R^9$ and $R^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
$E^1$ represents $NR^{18}$,
in which
$R^{18}$ represents hydrogen,
$E^2$ represents N,
$E^3$ represents $CR^{19}$,
in which
$R^{19}$ represents hydrogen, trifluoromethyl, ($C_1$-$C_4$)-alkyl or a group of the formula -M-$R^{13}$, in which (C$_1$-C$_4$)-alkyl may be substituted by 1 to 3 substituents independently of one another selected from the group consisting of fluorine, trifluoromethyl, cyclopropyl and cyclobutyl,
and in which
M represents a bond,
R$^{13}$ represents —(C=O)$_r$—OR$^{14}$ or —(C=O)$_r$—NR$^{14}$R$^{15}$,
in which
r represents the number 0,
R$^{14}$ and R$^{15}$ independently of one another each represent hydrogen, methyl, ethyl, cyclopropyl or cyclobutyl,
U represents C(=O),
V represents NR$^{24}$,
in which
R$^{24}$ represents (C$_1$-C$_6$)-alkyl,
in which (C$_1$-C$_6$)-alkyl may itself be substituted by 1 to 3 substituents independently of one another selected from the group consisting of fluorine, trifluoromethyl, cyclopropyl, cyclobutyl and hydroxy,
R$^{23}$ represents hydrogen,
and their salts, solvates and solvates of the salts.

Preference is given in the context of the present invention to compounds of the formula (I) in which
the ring Q represents a group of the formula

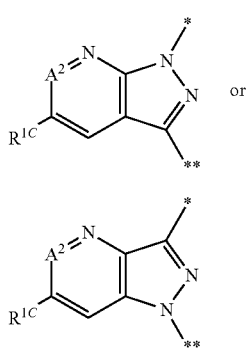

where
* represents the point of attachment to —CH$_2$—R$^2$,
** represents the point of attachment to R$^3$,
R$^{1C}$ represents hydrogen or fluorine,
A$^2$ represents CH,
R$^2$ represents 3,3,3-trifluoroprop-1-yl, 2,2,3,3-tetrafluoroprop-1-yl, 2,2,3,3,3-pentafluoroprop-1-yl, phenyl, pyridyl or pyrimidinyl,
where phenyl is substituted by 1 to 3 fluorine substituents, and
where pyridyl and pyrimidinyl may be substituted by 1 fluorine substituent,
R$^3$ represents a group of the formula

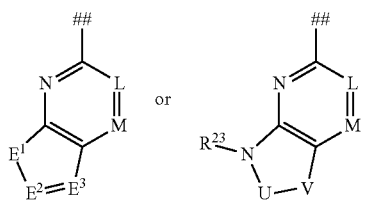

where
## represents the point of attachment to the ring Q,
L represents N,
M represents CR$^4$,
in which
R$^4$ represents —R$^5$, —OR$^6$ or —NR$^7$R$^8$,
in which
R$^5$ represents trifluoromethyl or (C$_1$-C$_4$)-alkyl,
in which (C$_1$-C$_4$)-alkyl for its part may be substituted by 1 or 2 substituents independently of one another selected from the group consisting of trifluoromethyl, cyclopropyl, cyclobutyl, difluoromethoxy, trifluoromethoxy, —(C=O)$_p$—OR$^9$ and —C(=O)$_p$—NR$^9$R$^{10}$,
in which
p represents the number 0,
R$^9$ and R$^{10}$ independently of one another each represent methyl, ethyl, trifluoromethyl, 2,2,2-trifluoroethyl, 1,1,2,2,2-pentafluoroethyl, cyclopropyl or cyclobutyl,
or
R$^9$ and R$^{10}$ together with the atom(s) to which they are respectively attached form a pyrrolidinyl, piperidinyl, piperazinyl or morpholinyl ring,
in which the pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
R$^6$ represents (C$_1$-C$_6$)-alkyl or pyrazolyl,
in which (C$_1$-C$_6$)-alkyl may be substituted by 1 to 3 substituents independently of one another selected from the group consisting of trifluoromethyl, cyclopropyl, cyclobutyl, cyclopentyl, difluoromethoxy, trifluoromethoxy, (C$_1$-C$_4$)-alkoxy, —(C=O)—OR$^9$ and —(C=O)—NR$^9$R$^{10}$,
in which
R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
and
in which pyrazolyl may be substituted by 1 to 3 substituents independently of one another selected from the group consisting of fluorine, difluoromethyl, trifluoromethyl, 2,2,2-trifluoroethyl, 1,1,2,2-pentafluoroethyl, methyl, cyclopropyl, cyclobutyl and cyclopentyl,
R$^7$ represents hydrogen, methyl or ethyl,
R$^8$ represents (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C$_1$-C$_6$)-alkyl may be substituted by 1 to 3 substituents independently of one another selected from the group consisting of trifluoromethyl, cyclopropyl, cyclobutyl, trifluoromethoxy, (C$_1$-C$_4$)-alkoxy, tetrahydrofuranyl, pyrrolidinyl, tetrahydropyranyl, phenyl, furanyl, pyrazolyl, imidazolyl, triazolyl and pyridyl,
in which tetrahydrofuranyl, pyrrolidinyl, tetrahydropyranyl, phenyl, furanyl, pyrazolyl, imidazolyl, triazolyl and pyridyl for their part may be substituted by 1 or 2 substituents independently of one another selected from the group consisting of fluorine, chlorine, cyano, difluoromethyl, trifluoromethyl, methyl, ethyl, oxo, difluoromethoxy, trifluoromethoxy, methoxy and ethoxy, and in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl, trifluoromethoxy and oxo, $E^1$ represents $NR^{18}$,
in which
$R^{18}$ represents hydrogen,
$E^2$ represents N,
$E^3$ represents N or $CR^{19}$,
in which
$R^{19}$ represents hydrogen, fluorine, difluoromethyl, trifluoromethyl, $(C_1-C_4)$-alkyl or a group of the formula $-M-R^{13}$,
in which $(C_1-C_4)$-alkyl may be substituted by 1 to 3 substituents independently of one another selected from the group consisting of fluorine, trifluoromethyl, cyclopropyl and cyclobutyl,
and in which
M represents a bond, methylene, ethane-1,2-diyl or propane-1,3-diyl,
$R^{13}$ represents $-(C=O)_r-OR^{14}$, $-(C=O)_r-NR^{14}R^{15}$, phenyl, thiazolyl, triazolyl, oxadiazolyl, thiadiazolyl or pyrimidinyl,
in which
r represents the number 0 or 1,
$R^{14}$ and $R^{15}$ independently of one another each represent hydrogen, methyl, ethyl, cyclopropyl, cyclobutyl or phenyl,
in which methyl and ethyl may additionally be substituted by 1 or 2 substituents independently of one another selected from the group consisting of fluorine, difluoromethyl, trifluoromethyl, cyclopropyl, cyclobutyl, hydroxy, trifluoromethoxy and methoxy,
and
in which phenyl, thiazolyl, triazolyl, oxadiazolyl, thiadiazolyl and pyrimidinyl may each in turn be substituted by 1 or 2 substituents selected independently of one another from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
U represents $C(=O)$,
V represents $NR^{24}$,
in which
$R^{24}$ represents trideuteromethyl, $(C_1-C_6)$-alkyl, cyclopropyl, cyclobutyl, azetidin-3-yl, pyrrolidin-3-yl or piperidin-4-yl,
in which $(C_1-C_6)$-alkyl for its part may be substituted by 1 to 3 substituents independently of one another selected from the group consisting of fluorine, trifluoromethyl, cyclopropyl, cyclobutyl, hydroxy, oxetanyl and morpholin-4-yl, and
in which azetidin-3-yl, pyrrolidin-3-yl and piperidin-4-yl for their part may be substituted by 1 or 2 substituents independently of one another selected from the group consisting of fluorine, trifluoromethyl, 2,2-difluoroethyl, 2,2,2-trifluoroethyl, cyclopropyl and cyclobutyl,
$R^{23}$ represents hydrogen,
and their salts, solvates and solvates of the salts.

In the context of the present invention, preference is also given to compounds of the formula (I) in which
$R^3$ represents a group of the formula

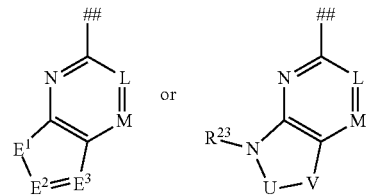

where
## represents the point of attachment to the ring Q,
L represents N,
M represents $CR^1$,
in which
$R^4$ represents $-R^5$ or $-NR^7R^8$,
in which
$R^5$ represents hydrogen,
$R^7$ represents hydrogen,
$R^8$ represents hydrogen or $(C_1-C_6)$-alkyl,
in which $(C_1-C_6)$-alkyl is substituted by 1 to 3 substituents independently of one another selected from the group consisting of fluorine, trifluoromethyl, cyclopropyl, cyclobutyl, $-(C=O)_p-OR^9$ and $-C(=O)_p-NR^9R^{10}$,
in which
p represents the number 0,
$R^9$ and $R^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
$E^1$ represents $NR^{18}$,
in which
$R^{18}$ represents hydrogen,
$E^2$ represents N,
$E^3$ represents $CR^{19}$,
in which
$R^{19}$ represents hydrogen, trifluoromethyl, $(C_1-C_4)$-alkyl or a group of the formula $-M-R^{13}$,
in which $(C_1-C_4)$-alkyl may be substituted by 1 to 3 substituents independently of one another selected from the group consisting of fluorine, trifluoromethyl, cyclopropyl and cyclobutyl,
and in which
M represents a bond,
$R^{13}$ represents $-(C=O)_r-OR^{14}$ or $-(C=O)_r-NR^{14}R^{15}$,
in which
r represents the number 0,
$R^{14}$ and $R^{15}$ independently of one another each represent hydrogen, methyl, ethyl, cyclopropyl or cyclobutyl,
U represents $C(=O)$,
V represents $NR^{24}$, in which
R$^{24}$ represents (C$_1$-C$_6$)-alkyl,
in which (C$_1$-C$_6$)-alkyl may itself be substituted by 1 to 3 substituents independently of one another selected from the group consisting of fluorine, trifluoromethyl, cyclopropyl, cyclobutyl and hydroxy,
R$^{23}$ represents hydrogen,
and their salts, solvates and solvates of the salts.

In the context of the present invention, preference is also given to compounds of the formula (I) in which
the ring Q represents a group of the formula

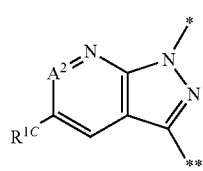

(a-1-2)

where
* represents the point of attachment to —CH$_2$—R$^2$,
** represents the point of attachment to R$^3$,
R$^{1C}$ represents hydrogen or fluorine,
A$^2$ represents CH,
and their salts, solvates and solvates of the salts.

In the context of the present invention, preference is also given to compounds of the formula (I) in which
R$^2$ represents 3,3,3-trifluoroprop-1-yl, 2,2,3,3-tetrafluoroprop-1-yl, 2,2,3,3,3-pentafluoroprop-1-yl, phenyl, pyridyl or pyrimidinyl,
where phenyl is substituted by 1 to 3 fluorine substituents, and
where pyridyl and pyrimidinyl may be substituted by 1 fluorine substituent,
R$^3$ represents a group of the formula

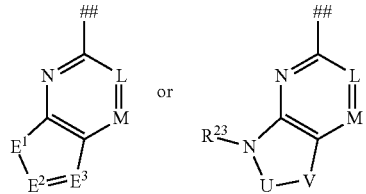

where
## represents the point of attachment to the ring Q,
L represents N,
M represents CR$^4$,
in which
R$^4$ represents —R$^5$, —OR$^6$ or —NR$^7$R$^8$,
in which
R$^5$ represents trifluoromethyl or (C$_1$-C$_4$)-alkyl,
in which (C$_1$-C$_4$)-alkyl for its part may be substituted by 1 or 2 substituents independently of one another selected from the group consisting of trifluoromethyl, cyclopropyl, cyclobutyl, difluoromethoxy, trifluoromethoxy, —(C=O)$_p$—OR$^9$ and —C(=O)$_p$—NR$^9$R$^{10}$,
in which
p represents the number 0,
R$^9$ and R$^{10}$ independently of one another each represent methyl, ethyl, trifluoromethyl, 2,2,2-trifluoroethyl, 1,1,2,2,2-pentafluoroethyl, cyclopropyl or cyclobutyl,
or
R$^9$ and R$^{10}$ together with the atom(s) to which they are respectively attached form a pyrrolidinyl, piperidinyl, piperazinyl or morpholinyl ring,
in which the pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
R$^6$ represents (C$_1$-C$_6$)-alkyl or pyrazolyl,
in which (C$_1$-C$_6$)-alkyl may be substituted by 1 to 3 substituents independently of one another selected from the group consisting of trifluoromethyl, cyclopropyl, cyclobutyl, cyclopentyl, difluoromethoxy, trifluoromethoxy, (C$_1$-C$_4$)-alkoxy, —(C=O)—OR$^9$ and —(C=O)—NR$^9$R$^{10}$,
in which
R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
and
in which pyrazolyl may be substituted by 1 to 3 substituents independently of one another selected from the group consisting of fluorine, difluoromethyl, trifluoromethyl, 2,2,2-trifluoroethyl, 1,1,2,2-pentafluoroethyl, methyl, cyclopropyl, cyclobutyl and cyclopentyl,
R$^7$ represents hydrogen, methyl or ethyl,
R$^8$ represents (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
in which (C$_1$-C$_6$)-alkyl may be substituted by 1 to 3 substituents independently of one another selected from the group consisting of trifluoromethyl, cyclopropyl, cyclobutyl, trifluoromethoxy, (C$_1$-C$_4$)-alkoxy, tetrahydrofuranyl, pyrrolidinyl, tetrahydropyranyl, phenyl, furanyl, pyrazolyl, imidazolyl, triazolyl and pyridyl,
in which tetrahydrofuranyl, pyrrolidinyl, tetrahydropyranyl, phenyl, furanyl, pyrazolyl, imidazolyl, triazolyl and pyridyl for their part may be substituted by 1 or 2 substituents independently of one another selected from the group consisting of fluorine, chlorine, cyano, difluoromethyl, trifluoromethyl, methyl, ethyl, oxo, difluoromethoxy, trifluoromethoxy, methoxy and ethoxy,
and
in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl, trifluoromethoxy and oxo,
E$^1$ represents NR$^{18}$,
in which
R$^{18}$ represents hydrogen,
E$^2$ represents N, $E^3$ represents N or $CR^{19}$, in which $R^{19}$ represents hydrogen, fluorine, difluoromethyl, trifluoromethyl, $(C_1-C_4)$-alkyl or a group of the formula -M-$R^{13}$, in which $(C_1-C_4)$-alkyl may be substituted by 1 to 3 substituents independently of one another selected from the group consisting of fluorine, trifluoromethyl, cyclopropyl and cyclobutyl, and in which M represents a bond, methylene, ethane-1,2-diyl or propane-1,3-diyl, $R^{13}$ represents —(C=O)$_r$—$OR^{14}$, —(C=O)$_r$— $NR^{14}R^{15}$, phenyl, thiazolyl, triazolyl, oxadiazolyl, thiadiazolyl or pyrimidinyl, in which r represents the number 0 or 1, $R^{14}$ and $R^{15}$ independently of one another each represent hydrogen, methyl, ethyl, cyclopropyl, cyclobutyl or phenyl, in which methyl and ethyl may additionally be substituted by 1 or 2 substituents independently of one another selected from the group consisting of fluorine, difluoromethyl, trifluoromethyl, cyclopropyl, cyclobutyl, hydroxy, trifluoromethoxy and methoxy, and in which phenyl, thiazolyl, triazolyl, oxadiazolyl, thiadiazolyl and pyrimidinyl may each in turn be substituted by 1 or 2 substituents selected independently from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl, U represents C(=O), V represents $NR^{24}$, in which $R^{24}$ represents trideuteromethyl, $(C_1-C_6)$-alkyl, cyclopropyl, cyclobutyl, azetidin-3-yl, pyrrolidin-3-yl or piperidin-4-yl, in which $(C_1-C_6)$-alkyl for its part may be substituted by 1 to 3 substituents independently of one another selected from the group consisting of fluorine, trifluoromethyl, cyclopropyl, cyclobutyl, hydroxy, oxetanyl and morpholin-4-yl, and in which azetidin-3-yl, pyrrolidin-3-yl and piperidin-4-yl for their part may be substituted by 1 or 2 substituents independently of one another selected from the group consisting of fluorine, trifluoromethyl, 2,2-difluoroethyl, 2,2,2-trifluoroethyl, cyclopropyl and cyclobutyl, $R^{23}$ represents hydrogen, and their salts, solvates and solvates of the salts.

In the context of the present invention, preference is also given to compounds of the formula (I) in which $R^2$ is 3,3,3-trifluoroprop-1-yl, 2,2,3,3-tetrafluoroprop-1-yl, 2,2,3,3,3-pentafluoroprop-1-yl, 2-fluorophenyl or 3-fluoropyrid-2-yl, $R^3$ represents a group of the formula

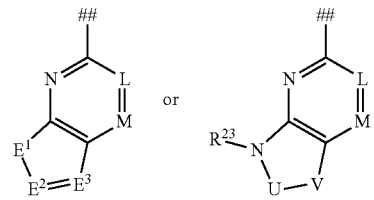

where ## represents the point of attachment to the ring Q,

L represents N,

M represents $CR^4$, in which $R^4$ represents —$NR^7R^8$, in which $R^7$ represents hydrogen or methyl, $R^8$ represents $(C_1-C_6)$-alkyl, in which $(C_1-C_6)$-alkyl may be substituted by 1 to 3 substituents independently of one another selected from the group consisting of trifluoromethyl, cyclopropyl, cyclobutyl, trifluoromethoxy and $(C_1-C_4)$-alkoxy, $E^1$ represents $NR^{18}$, in which $R^{18}$ represents hydrogen, $E^2$ represents N, $E^3$ represents $CR^{19}$, in which $R^{19}$ represents hydrogen, trifluoromethyl, $(C_1-C_4)$-alkyl or a group of the formula -M-$R^{13}$, in which $(C_1-C_4)$-alkyl may be substituted by 1 to 3 substituents independently of one another selected from the group consisting of fluorine, trifluoromethyl, cyclopropyl and cyclobutyl, and in which M represents a bond, $R^{13}$ represents —(C=O)$_r$$OR^{14}$ or —(C=O)$_r$— $NR^{14}$—$R^{15}$, in which r represents the number 0, $R^{14}$ and $R^{15}$ independently of one another each represent hydrogen, methyl, ethyl, cyclopropyl or cyclobutyl, in which methyl and ethyl may additionally be substituted by 1 or 2 substituents independently of one another selected from the group consisting of fluorine, difluoromethyl, trifluoromethyl, cyclopropyl, cyclobutyl, hydroxy, trifluoromethoxy and methoxy, U represents C(=O), V represents $NR^{24}$, in which $R^{24}$ represents $(C_1-C_6)$-alkyl, in which $(C_1-C_6)$-alkyl may itself be substituted by 1 to 3 substituents independently of one another selected from the group consisting of fluorine, trifluoromethyl, cyclopropyl, cyclobutyl and hydroxy, $R^{23}$ represents hydrogen, and their salts, solvates and solvates of the salts.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the compounds of the formula (I) according to the invention, characterized in that

[A] a compound of the formula (II)

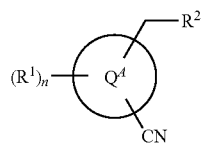
(II)

in which R² has the meaning given above and the ring Q⁴ represents a group of the formula

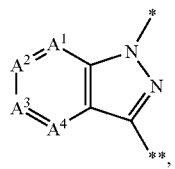
(a-1)

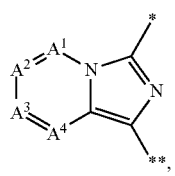
(c-1)

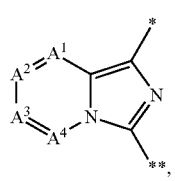
(d-1)

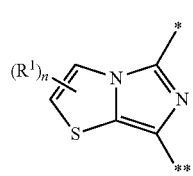
(g-1)

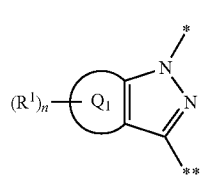
(l-1)

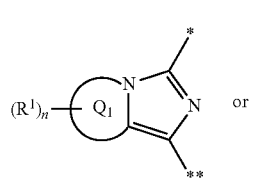
(n-1) or

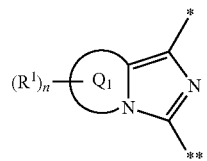
(o-1)

where
* represents the point of attachment to —CH₂—R²,
** represents the point of attachment to R³,
the ring Q₁ together with the atoms to which it is attached forms a 5- to 7-membered saturated or partially unsaturated carbocycle or a 5- to 7-membered saturated or partially unsaturated heterocycle,
R¹ represents fluorine, chlorine, methyl, hydroxy or oxo,
n represents a number 0, 1 or 2,
A¹, A², A³ and A⁴ independently of one another each represent N, CH or CR¹,
with the proviso that not more than two of the A¹, A², A³ and A⁴ groups represent N,
is reacted in an inert solvent in the presence of a suitable base with a compound of the formula (III-1) or (III-2)

(III-1)

or

(III-2)

in which G¹, G², G³, G⁴, E¹, E² and E³ each have the meanings given above,
to give a compound of the formula (I-A-1) or (I-A-2)

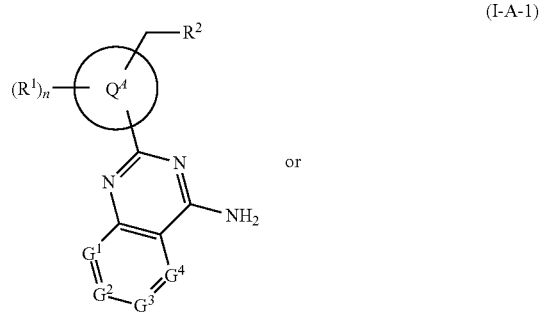
(I-A-1)

or

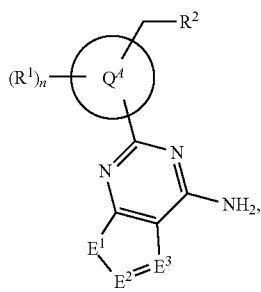

(I-A-2)

in which n, R$^1$, R$^2$, G$^1$, G$^2$, G$^3$, G$^4$, E$^1$, E$^2$, E$^3$ and Q$^4$ each have the meanings given above, or

[B] a compound of the formula (I-B-1) or (I-B-2)

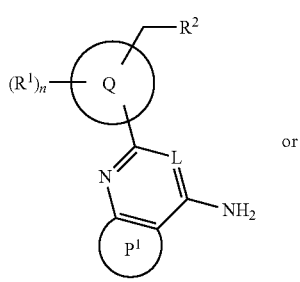

(I-B-1)

or

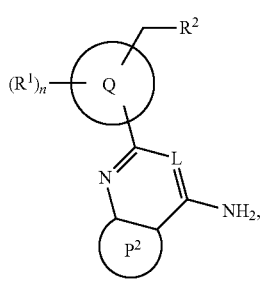

(I-B-2)

in which n, P$^1$, P$^2$, R$^1$, R$^2$ and Q each have the meanings given above, is reacted in an inert solvent with a suitable nitrite to give a compound of the formula (I-I-3) or (I-I-4)

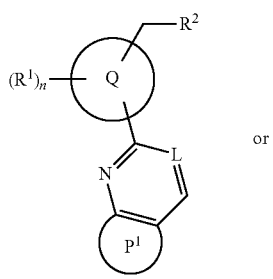

(I-B-3)

or

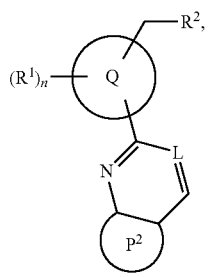

(I-B-4)

in which n, P$^1$, P$^2$, R$^1$, R$^2$ and Q each have the meanings given above, or

[C] a compound of the formula (I-B-1) or (I-B-2) is converted in an inert solvent into a compound of the formula (IV-1) or (IV-2)

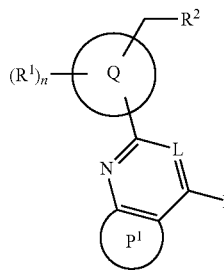

(IV-1)

or

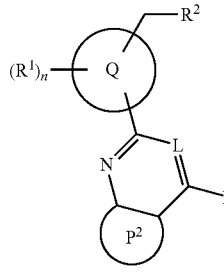

(IV-2)

in which n, P$^1$, P$^2$, R$^1$, R$^2$ and Q each have the meanings given above and X$^2$ represents bromine, iodine or chlorine, and this is then reacted in an inert solvent, optionally in the presence of a suitable base, with a compound of the formula (V)

$$R^{44}\text{—H} \quad (V)$$

in which

R$^4$ represents —OR$^6$ or —NR$^7$R$^8$, where R$^6$, R$^7$ and R$^8$ each have the meanings given above, to give a compound of the formula (I-C-1) or (I-C-2)

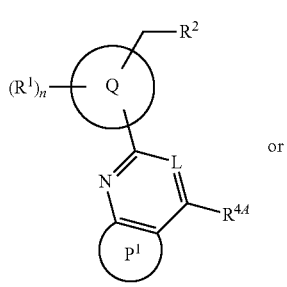
(I-C-1)

or

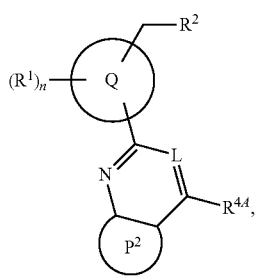
(I-C-2)

in which n, P$^1$, P$^2$, R$^1$, R$^2$, R$^{4A}$ and Q each have the meanings given above, or

[D] a compound of the formula (VI)

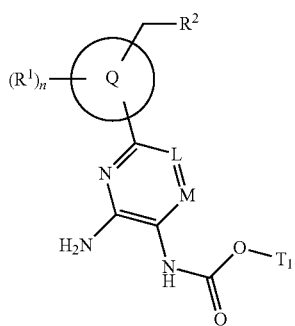
(VI)

in which n, Q, R$^1$ and R$^2$ are each as defined above and T$^1$ represents (C$_1$-C$_4$)-alkyl is reacted in an inert solvent in the presence of a suitable base with a compound of the formula (VII)

R$^{24A}$—X$^1$ (VII)

in which

R$^{24A}$ represents trideuteromethyl, (C$_1$-C$_6$)-alkyl, (C$_2$-C$_6$)-alkenyl, (C$_3$-C$_7$)-cycloalkyl, azetidinyl, pyrrolidinyl, piperidinyl or benzyl, in which (C$_1$-C$_6$)-alkyl, azetidinyl, pyrrolidinyl, piperidinyl and benzyl may be substituted within the scope of the meaning given above, and X$^1$ represents a suitable leaving group, for example halogen, especially chlorine or bromine, mesylate or tosylate, to give a compound of the formula (VIII)

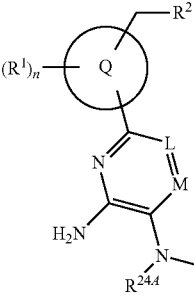
(VIII)

in which n, Q, R$^1$, R$^2$ and R$^{24A}$ each have the meanings above, and this is then cyclized in an inert solvent in the presence of a suitable base to give a compound of the formula (I-D)

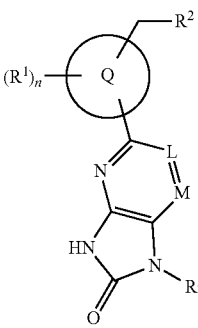
(I-D)

in which n, Q, R$^1$, R$^2$ and R$^{24A}$ each have the meanings above, and any protecting groups present are detached by methods known to those skilled in the art, and the resulting compounds of the formula (I) are optionally converted optionally with the appropriate (i) solvents and/or (ii) acids or bases to the solvates, salts and/or solvates of the salts thereof.

Inert solvents for the process step (II)+(III-1)→(I-A-1) or (II)+(III-2)→(I-A-2) are, for example, halogenated hydrocarbons and hydrocarbons such as benzene, toluene, xylene, hexane, cyclohexane or mineral oil fractions, or other solvents such as acetone, methyl ethyl ketone, ethyl acetate, acetonitrile, N,N-dimethylformamide (DMF), dimethyl sulphoxide (DMSO), N,N'-dimethylpropyleneurea (DMPU), N-methylpyrrolidone (NMP), sulpholane or pyridine. It is also possible to use mixtures of the solvents mentioned. Preference is given to using DMF.

Suitable bases for the process step (II)+(III-1)→(I-A-1) or (II)+(III-2)→(I-A-2) are the customary inorganic or organic bases. These preferably include alkali metal alkoxides such as sodium or potassium methoxide, sodium or potassium ethoxide or sodium or potassium tert-butoxide, alkali metal hydrides such as sodium or potassium hydride, or amides such as sodium amide, lithium or potassium bis(trimethylsilyl)amide or lithium diisopropylamide. Preference is given to using potassium tert-butoxide.

The process step (II)+(III-1)→(I-A-1) or (II)+(III-2)→(I-A-2) is generally performed within a temperature range from +100° C. to +200° C., preferably at +140° C. to +180° C., preferably in a microwave. The conversion can be carried out at atmospheric, elevated or reduced pressure (for example from 0.5 to 5 bar).

Suitable nitrites for the conversions (I-B-1) or (I-B-2)→(I-B-3) or (I-B-4) are, for example, sodium nitrite, isopentyl nitrite or tert-butyl nitrite.

Inert solvents for the conversions (I-B-1) or (I-B-2)→(I-B-3) or (I-B-4) are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to tetrahydrofuran or DMF.

The reactions (I-B-1) or (I-B-2)→(I-B-3) or (I-B-4) are generally performed within a temperature range from 0° C. to +120° C., preferably at +40° C. to +80° C. The conversion can be carried out at atmospheric, elevated or reduced pressure (for example from 0.5 to 5 bar). The reaction is generally carried out at atmospheric pressure.

The process step (I-B-1)→(IV-1) or (I-B-2)→(IV-2) is carried out with or without solvents. Suitable solvents are all organic solvents which are inert under the reaction conditions. The preferred solvent is dimethoxyethane.

The reaction (I-B-1)→(IV-1) or (I-B-2)→(IV-2) is generally carried out within a temperature range from +20° C. to +100° C., preferably within the range from +50° C. to +100° C., optionally in a microwave. The conversion can be carried out at atmospheric, elevated or reduced pressure (for example in the range from 0.5 to 5 bar). The reaction is generally carried out at atmospheric pressure.

The process step (I-B-1)→(IV-1) or (I-B-2)→(IV-2) is generally carried out using a molar ratio of 10 to 30 mol of isopentyl nitrite and 10 to 30 mol of the iodine equivalent based on 1 mol of the compound of the formula (I-B-1) or (I-B-2).

Suitable halogen sources in the conversion (I-B-1)→(IV-1) or (I-B-2)→(IV-2) are, for example, diiodomethane, a mixture of caesium iodide, iodine and copper(I) iodide or copper(II) bromide and also phosphoryl chloride.

Inert solvents for the process step (I-B-1)→(I-B-3) or (I-B-2)→(I-B-4) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction (I-B-1)→(I-B-3) or (I-B-2)→(I-B-4) is carried out using hydrogen in conjunction with transition metal catalysts, for example palladium (10% on activated carbon), Raney nickel or palladium hydroxide.

The reaction (I-B-1)→(I-B-3) or (I-B-2)→(I-B-4) is generally carried out within a temperature range from +20° C. to +50° C. The conversion can be carried out at atmospheric or elevated pressure (for example in the range from 0.5 to 5 bar). The reaction is generally carried out at atmospheric pressure.

Inert solvents for the process step (IV-1) or (IV-2)+(V)→(I-C-1) or (I-C-2) are, for example, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is also possible to use mixtures of the solvents mentioned. Preference is given to NMP.

In the case of $R^{4A}$=—$OR^6$, the reaction (IV-1) or (IV-2)+(V)→(I-C-1) or (I-C-2) is preferably carried out in the absence of a solvent.

In the case of $R^{4A}$=—$OR^6$, the reaction (IV-1) or (IV-2)+(V)→(I-C-1) or (I-C-2) is carried out in the presence of a suitable copper catalyst such as, for example, copper(I) iodide, with addition of 3,4,7,8-tetramethyl-1,10-phenanthroline, and a suitable base such as, for example, alkaline earth metal carbonates such as lithium carbonate, sodium carbonate, potassium carbonate, calcium carbonate or caesium carbonate, preferably caesium carbonate.

Alternatively, in the case of $R^{4A}$=—$OR^6$ the preparation of the compounds of the formula (I-C-1) or (I-C-2) can also be carried out under Mitsunobu conditions [see: a) Hughes, D. L. "The Mitsunobu Reaction," *Organic Reactions*; John Wiley & Sons, Ltd, 1992, vol. 42, p. 335. b) Hughes, D. L. *Org. Prep. Proceed. Int.* 1996, 28, 127.] starting with a compound of the formula (IX-1) or (IX-2)

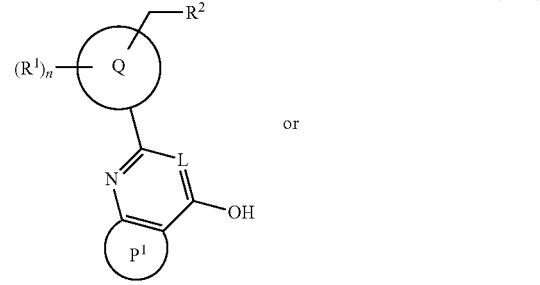

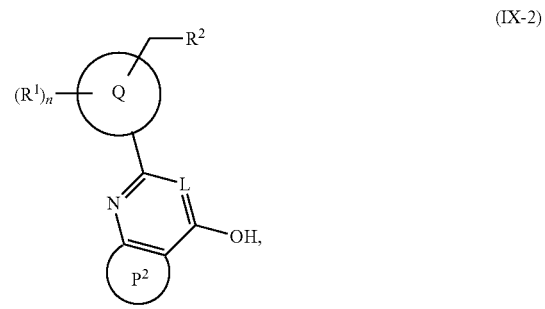

in which n, L, Q, $P^1$, $P^2$, $R^1$ and $R^2$ are each as defined above.

Here, the Mitsunobu reaction is carried out using triphenylphosphine, or tri-n-butylphosphine, 1,2-bis(diphenylphosphino)ethane (DPPE), diphenyl(2-pyridyl)phosphine (Ph2P-Py), (p-dimethylaminophenyl)diphenylphosphine (DAP-DP), tris(4-dimethylaminophenyl)phosphine (tris-DAP), and a suitable dialkyl azodicarboxylate, for example diethyl azodicarboxylate (DEAD), diisopropyl azodicarboxylate (DIAD), di-tert-butyl azodicarboxylate, N,N,N'N'-tetramethylazodicarboxamide (TMAD), 1,1'-(azodicarbonyl)dipiperidine (ADDP) or 4,7-dimethyl-3,5,7-hexahydro-1,2,4,7-tetrazocine-3,8-dione (DHTD). Preference is given to using triphenylphosphine and diisopropyl azodicarboxylate (DIAD), or a suitable azodicarboxamide such as, for example, N,N,N',N'-tetramethyldiazene-1,2-dicarboxamide.

Inert solvents for the Mitsunobu reaction (IV-1) or (IV-2)+(V)→(I-C-1) or (I-C-2) are, for example, ethers such as tetrahydrofuran, diethyl ether, hydrocarbons such as benzene, toluene, xylene, halohydrocarbons such as dichloromethane, dichloroethane or other solvents such as acetonitrile, DMF or NMP. It is also possible to use mixtures of the solvents mentioned. Preference is given to using THF.

The Mitsunobu reaction (IV-1) or (IV-2)+(V)→(I-C-1) or (I-C-2) is generally carried out in a temperature range from −78° C. to +180° C., preferably at 0° C. to +50° C., optionally in a microwave. The conversions can be performed at atmospheric, elevated or reduced pressure (for example from 0.5 to 5 bar).

In the case of $R^{4,4}$=—$NR^7R^8$, if $R^7$ and $R^8$ together with the nitrogen atom to which they are attached form a 5- or 6-membered heteroaryl, which may be substituted within the scope of the meaning given above, the conversion (IV-1) or (IV-2)+(V)→(I-C-1) or (I-C-2) is carried out in the presence of a suitable copper catalyst such as, for example, copper(I) oxide, with addition of 2-hydroxybenzaldehyde oxime, and a suitable base such as, for example, alkaline earth metal carbonates such as lithium carbonate, sodium carbonate, potassium carbonate, calcium carbonate or caesium carbonate, preferably caesium carbonate.

The reaction (IV-1) or (IV-2)+(V)→(I-C-1) or (I-C-2) is generally carried out in a temperature range from +20° C. to +200° C., preferably at +150° C. to +200° C., preferably in a microwave. The conversion can be carried out at atmospheric, elevated or reduced pressure (for example from 0.5 to 5 bar).

Suitable inert solvents for the cyclization (VIII)→(I-D) are ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), dimethylacetamide, N-methylpyrrolidone (NMP), pyridine, acetonitrile or sulpholane. It is also possible to use mixtures of the solvents mentioned. Preference is given to tetrahydrofuran.

Suitable bases for the cyclization (VIII)→(I-D) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium bis(trimethylsilyl)amide.

The reaction (VIII)→(I-D) is generally conducted within a temperature range of −10° C. to +80° C., preferably at +10° C. to +30° C. The conversion can be carried out at atmospheric, elevated or reduced pressure (for example from 0.5 to 5 bar). The reaction is generally carried out at atmospheric pressure.

Inert solvents for the reaction (VI)+(VII)→(VIII) are ethers such as diethyl ether, dioxane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), dimethylacetamide, N-methylpyrrolidone (NMP), pyridine, acetonitrile or sulpholane. It is also possible to use mixtures of the solvents mentioned. Preference is given to tetrahydrofuran.

Suitable bases for the reaction (VI)+(VII)→(VIII) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate, calcium carbonate or caesium carbonate, alkali metal alkoxides such as sodium methoxide or potassium methoxide, sodium ethoxide or potassium ethoxide or sodium or potassium tert-butoxide, alkali metal hydrides such as sodium hydride or potassium hydride, amides such as sodium amide, lithium bis(trimethylsilyl)amide, sodium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium hydride.

The reaction (VI)+(VII)→(VIII) is generally carried out in a temperature range from −10° C. to +80° C., preferably from +10° C. to +30° C. The conversion can be carried out at atmospheric, elevated or reduced pressure (for example from 0.5 to 5 bar). The reaction is generally carried out at atmospheric pressure.

Suitable nitrites for the conversions (I-B-1) or (I-B-2)→(I-B-3) or (I-B-4) are, for example, sodium nitrite, isopentyl nitrite or tert-butyl nitrite.

Inert solvents for the conversions (I-B-1) or (I-B-2)→(I-B-3) or (I-B-4) are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. It is also possible to use mixtures of the solvents mentioned. Preference is given to tetrahydrofuran or DMF.

The reactions (I-B-1) or (I-B-2)→(I-B-3) or (I-B-4) are generally carried out in a temperature range from 0° C. to +120° C., preferably at +40° C. to +80° C. The conversion can be carried out at atmospheric, elevated or reduced pressure (for example from 0.5 to 5 bar). The reaction is generally carried out at atmospheric pressure.

The process step (I-B-1)→(IV-1) or (I-B-2)→(IV-2) is carried out with or without solvents. Suitable solvents are all organic solvents which are inert under the reaction conditions. The preferred solvent is dimethoxyethane.

The reaction (I-B-1)→(IV-1) or (I-B-2)→(IV-2) is generally carried out within a temperature range from +20° C. to +100° C., preferably within the range from +50° C. to +100° C., optionally in a microwave. The conversion can be carried out at atmospheric, elevated or reduced pressure (for example in the range from 0.5 to 5 bar). The reaction is generally carried out at atmospheric pressure.

The process step (I-B-1)→(IV-1) or (I-B-2)→(IV-2) is generally carried out using a molar ratio of 10 to 30 mol of isopentyl nitrite and 10 to 30 mol of the iodine equivalent based on 1 mol of the compound of the formula (I-B-1) or (I-B-2).

Examples of suitable iodine sources in the conversion (I-B-1)→(IV-1) or (I-B-2)→(IV-2) include diiodomethane or a mixture of caesium iodide, iodine and copper(I) iodide.

Inert solvents for the process step (I-B-1)→(I-B-3) or (I-B-2)→(I-B-4) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is also possible to use mixtures of the solvents mentioned. Preference is given to DMF.

The reduction (I-B-1)→(I-B-3) or (I-B-2)→(I-B-4) is carried out using hydrogen in conjunction with transition metal catalysts, for example palladium (10% on activated carbon), Raney nickel or palladium hydroxide.

The reaction (I-B-1)→(I-B-3) or (I-B-2)→(I-B-4) is generally carried out within a temperature range from +20° C. to +50° C. The conversion can be carried out at atmospheric or elevated pressure (for example in the range from 0.5 to 5 bar). The reaction is generally carried out at atmospheric pressure.

The preparation processes described above are illustrated by way of example by the following synthesis schemes (Schemes 1 and 2):

Scheme 1:

Scheme 2:

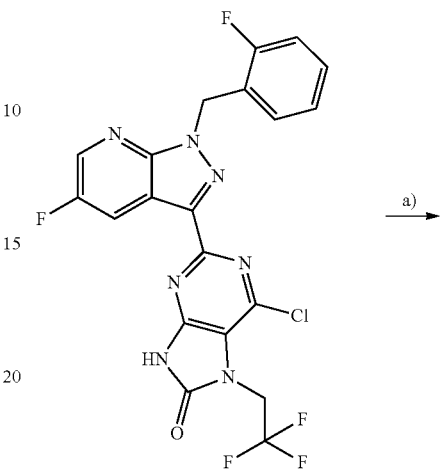

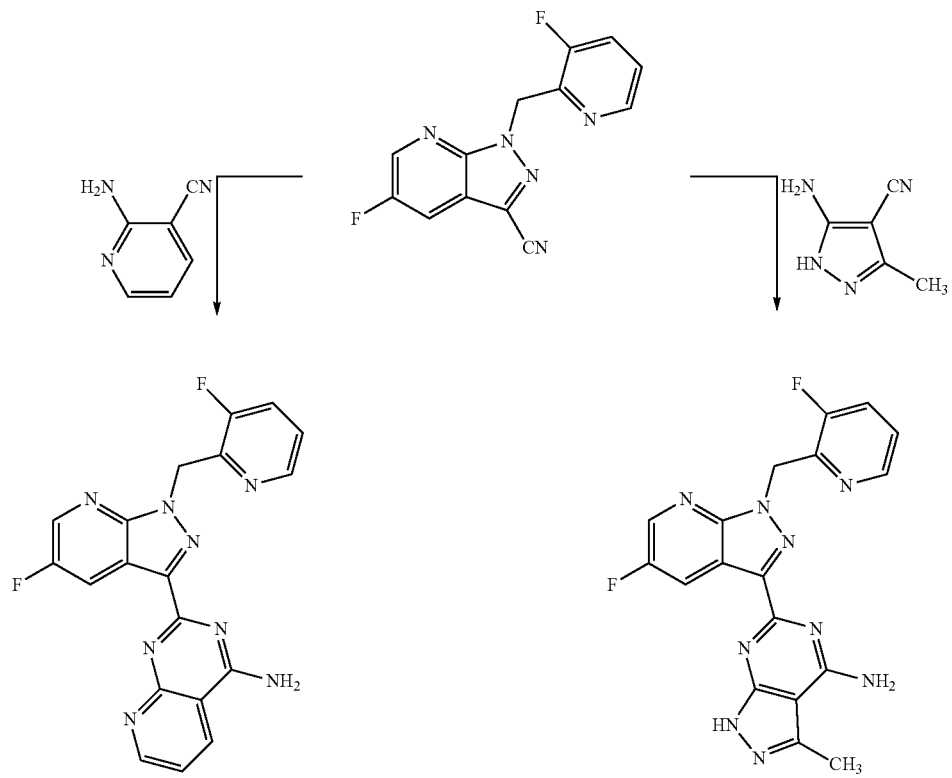

[potassium tert-butoxide, DMF, microwave, 160° C.].

-continued

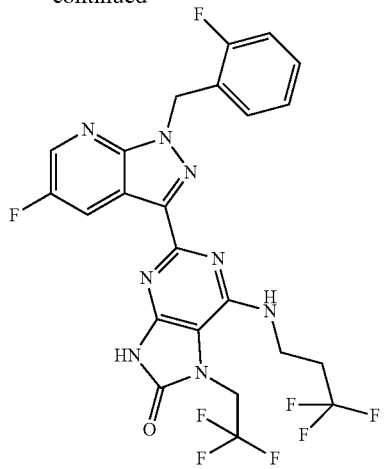

[a]: 3,3,3-trifluoropropyl-1-amine hydrochloride, N,N-diisopropylethylamine, NMP, microwave, 150° C.].

The compounds of the formulae (III-1), (III-2), (V) and (VII) are commercially available, known from the literature or can be prepared in analogy to literature processes.

The compounds of the formulae (II), (I-B-1), (I-B-2), (IV-1), (IV-2) and (VI) are known from the literature, can be prepared analogously to processes known from the literature or as described in the present experimental section.

The compounds according to the invention are potent stimulators of soluble guanylate cyclase, have valuable pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in humans and animals.

The compounds according to the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilatation, hyperphosphataemia and/or need for dialysis. The present invention also encompasses the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinisation, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulating cerebral blood flow and are thus effective agents for control of migraine. They are also suitable for prophylaxis and control of sequelae of cerebral infarction (cerebral apoplexy) such as stroke, cerebral ischaemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for production of a medicament for the treatment and/or prophylaxis of disorders, especially of the aforementioned disorders.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

- organic nitrates and NO donors, for example sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), for example inhibitors of phosphodiesterases (PDE) 1, 2 and/or 5, in particular PDE 5 inhibitors such as sildenafil, vardenafil and tadalafil;
- agents having antithrombotic activity, for example and with preference from the group of platelet aggregation inhibitors, of anticoagulants or of profibrinolytic substances;
- active compounds lowering blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
- active compounds altering lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein (a) antagonists.

In a preferred embodiment of the invention, the compounds according to the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, non-toxic, pharmaceutically suitable excipients, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with enteric coatings or coatings that dissolve in a delayed manner or are insoluble and control the release of the compound according to the invention), tablets or films/oblates, films/lyophilizates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active compound, nature of the preparation and time or interval over which administration takes place.

For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration figures for liquid/liquid solutions are each based on volume.

A. EXAMPLES

Abbreviations and Acronyms aq. aqueous solution
calc. calculated
DCI direct chemical ionization (in MS)
DMF dimethylformamide
DMSO dimethyl sulphoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC/MS liquid chromatography-coupled mass spectrometry
LiHMDS lithium hexamethyldisilazide
Me methyl
min minute(s)
MS mass spectrometry
NMR nuclear magnetic resonance spectrometry
Pd/C palladium on activated carbon (10%)
Ph phenyl
RT room temperature
$R_t$ retention time (in HPLC)
t-Bu tert-butyl
TFA trifluoroacetic acid
THF tetrahydrofuran
UV ultraviolet spectrometry
v/v ratio by volume (of a solution)
XPHOS dicyclohexyl(2',4',6'-triisopropylbiphenyl-2-yl)phosphine HPLC and LC/MS Methods:

Method 1 (LC-MS):

Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):

Instrument: Waters ACQUITY SQD UPLC System; column: Waters Acquity UPLC HSS T3 1.8µ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 3 (LC-MS):

Instrument: Micromass QuattroPremier with Waters UPLC Acquity; column: Thermo Hypersil GOLD 1.9µ, 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

General Procedures:

General Procedure 1:

In a microwave vessel with stirrer magnet, 1.0 eq of example 2A (100 mg, 0.369 mmol) was dissolved together with 1.0 eq of the appropriate aminonitrile and 1.0 eq of potassium tert-butoxide in dimethylformamide (2.5 ml), and the vessel was closed and heated at 160° C. under microwave irradiation for 2 h. This was followed by reaction analysis. In the case of incomplete conversion, a further 0.5 eq of potassium tert-butoxide was added and the mixture was heated again at 160° C. under microwave irradiation until complete conversion. The reaction mixture was purified by preparative HPLC (mobile phase: acetonitrile/water with 0.05% of formic acid, gradient).

General Procedure 2:

In a microwave vessel with stirrer magnet, 1.0 eq of example 2A (100 mg, 0.32 mmol) was dissolved together with 1.0 eq of the appropriate aminonitrile and 1.0 eq of potassium tert-butoxide in dimethylformamide (2 ml), and the vessel was closed and heated at 160° C. under microwave irradiation for 2 h. This was followed by reaction analysis. If required (cf. examples), further reagents were added and the mixture was heated again under microwave irradiation. The reaction mixture was purified by preparative HPLC (mobile phase: acetonitrile/water with 0.01% of formic acid, gradient).

Starting Materials and Intermediates

Example 1A

5-Fluoro-1-[(3-fluoropyridin-2-yl)methyl]-3-iodo-1H-pyrazolo[3,4-b]pyridine

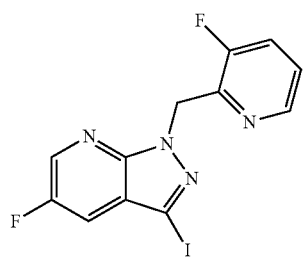 [SMILES: Fc1cnc2c(c1)c(I)nn2Cc1ncccc1F]

6.291 g (23.921 mmol) of 5-fluoro-3-iodo-1H-pyrazolo[3,4-b]pyridine (described in WO 2011/147809, Example 1, page 42) and 8.573 g (26.313 mmol) of caesium carbonate were initially charged in DMF (10 ml), and 5.00 g (26.313 mmol) of 2-(bromomethyl)-3-fluoropyridine dissolved in DMF (20 ml) were then added dropwise. The mixture was stirred at RT overnight. The mixture was then cooled and poured into 200 ml of water. A precipitate was filtered off with suction, washed with water and dried under high vacuum overnight. This gave 6.28 g (70% of theory) of the title compound.

LC-MS (Method 3): $R_t$=2.17 min
MS (ESIpos): m/z=373 (M+H)$^+$
$^1$H NMR (400 MHz; DMSO-$d_6$): δ=5.88 (s, 2H), 7.42-7.46 (m, 1H), 7.77 (dd, 1H), 7.93 (dd, 1H), 8.27 (d, 1H), 8.67 (t, 1H).

Example 2A

5-Fluoro-1-[(3-fluoropyridin-2-yl)methyl]-1H-pyrazolo[3,4-b]pyridine-3-carbonitrile

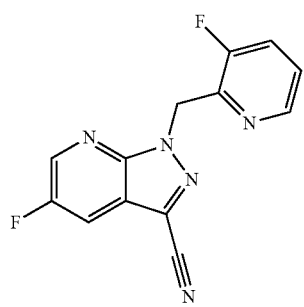 [SMILES: N#Cc1nn(Cc2ncccc2F)c2ncc(F)cc12]

6.280 g (16.876 mmol) of Example 1A and 1.663 g (18.564 mmol) of copper(I) cyanide were initially charged in DMSO (100 ml) and stirred at 150° C. for 3 h. After cooling, the reaction mixture was filtered through Celite and the filter cake was washed with ethyl acetate. The filtrate was extracted four times with saturated aqueous ammonium chloride solution and conc. aqueous ammonia (3:1 v/v), and the organic phase was separated off. The organic phase was then washed with saturated aqueous sodium chloride solution, dried over sodium sulphate, filtered and concentrated under reduced pressure. This gave 3.97 g (86% of theory) of the title compound.

LC-MS (Method 1): $R_t$=0.92 min
MS (ESIpos): m/z=272 (M+H)$^+$
$^1$H NMR (400 MHz; DMSO-$d_6$): δ=6.04 (s, 2H), 7.44-7.48 (m, 1H), 7.61 (t, 1H), 8.26 (d, 1H), 8.52 (dd, 1H), 8.83 (dd, 1H).

Example 3A

Methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate

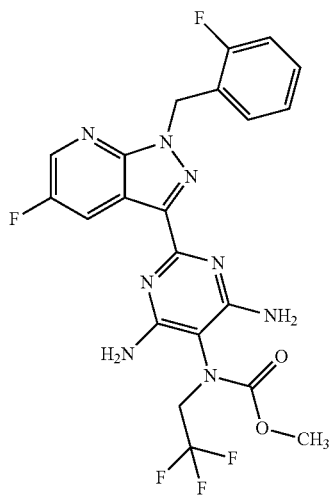 [SMILES: COC(=O)N(CC(F)(F)F)c1c(N)nc(-c2nn(Cc3ccccc3F)c3ncc(F)cc23)nc1N]

The synthesis of this compound is described in WO 2011/147809, Example 3, page 44.

Example 4A

6-Amino-2-[5-fluoro-1-(2-fluorobenzyl)-1H-pyrazolo[3,4-b]pyridin-3-yl]-7-(2,2,2-trifluoroethyl)-7,9-dihydro-8H-purin-8-one

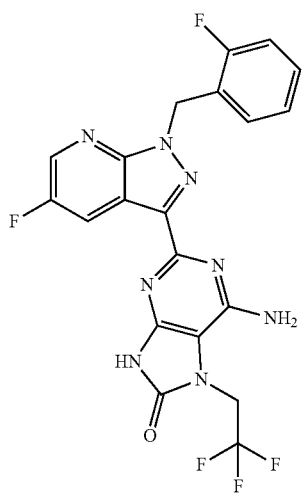 [SMILES: Nc1nc(-c2nn(Cc3ccccc3F)c3ncc(F)cc23)nc2[nH]c(=O)n(CC(F)(F)F)c12]

Under an argon atmosphere, 5.005 g (6.458 mmol) of the compound from Example 3A were dissolved in 355 ml of tetrahydrofuran and cooled to 0° C., and 16.145 ml (16.145 mmol) of a 1N solution of sodium bis(trimethylsilyl)amide in tetrahydrofuran were added dropwise. The mixture was stirred at 0° C. for 2 h and then at RT for 16 h. 16.145 ml (16.145 mmol) of 1N hydrochloric acid were added and the mixture was concentrated on a rotary evaporator. The residue was taken up in ethyl acetate and the organic phase was washed twice with water, dried over sodium sulphate and concentrated on a rotary evaporator. This gave 6.13 g of the title compound (purity by HPLC 61%). 500 mg of the residue were purified by preparative HPLC (mobile phase: methanol/water, gradient 30:70→90:10). This gave 93 mg of the title compound (36% of theory).

LC-MS (Method 1): $R_t$=1.01 min; MS (EIpos): m/z=477 [M+H]$^+$.

$^1$H NMR (400 MHz; DMSO-$d_6$): δ [ppm]=4.91 (q, 2H), 5.80 (s, 2H), 7.01 (s br, 2H), 7.13-7.18 (m, 1H), 7.21-7.26 (m, 2H), 7.34-7.40 (m, 1H), 8.70 (dd, 1H), 8.87 (dd, 1H), 11.96 (s, 1H).

Example 5A

2-[5-Fluoro-1-(2-fluorobenzyl)-1H-pyrazolo[3,4-b]pyridin-3-yl]-6-iodo-7-(2,2,2-trifluoroethyl)-7,9-dihydro-8H-purin-8-one

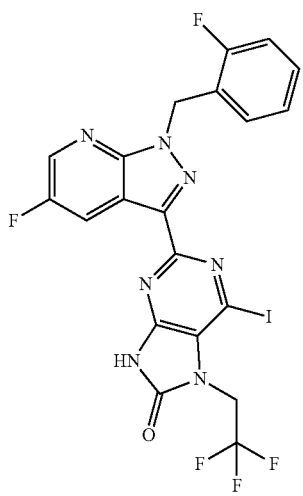 [SMILES: O=c1[nH]c2nc(-c3nn(Cc4ccccc4F)c4ncc(F)cc34)nc(I)c2n1CC(F)(F)F]

4.650 g (5.954 mmol) of the compound from Example 4A were dissolved in 12 ml of diiodomethane and 12.76 ml (95.270 mmol) of isopentyl nitrite were added. The reaction mixture was heated to 85° C. for 16 h and, after cooling, concentrated on a rotary evaporator. This gave 5 g of the crude product (purity 54%). 1.2 g of the residue were purified by preparative HPLC (mobile phase: acetonitrile/water with 0.05% formic acid, gradient 40:60→95:5). This gave 128 mg of the title compound (15% of theory).

LC-MS (Method 1): $R_t$=1.23 min; MS (EIpos): m/z=588 [M+H]$^+$.

$^1$H NMR (400 MHz; DMSO-$d_6$): δ [ppm]=4.95 (q, 2H), 5.86 (s, 2H), 7.14-7.18 (m, 1H), 7.21-7.27 (m, 2H), 7.35-7.41 (m, 1H), 8.47 (dd, 1H), 8.76 (dd, 1H), 12.79 (s, 1H).

Example 6A

6-Chloro-2-[5-fluoro-1-(2-fluorobenzyl)-1H-pyrazolo[3,4-b]pyridin-3-yl]-7-(2,2,2-trifluoroethyl)-7,9-dihydro-8H-purin-8-one

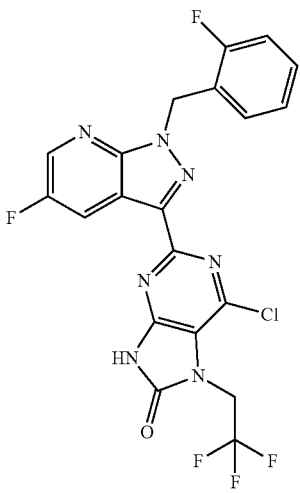 [SMILES: O=c1[nH]c2nc(-c3nn(Cc4ccccc4F)c4ncc(F)cc34)nc(Cl)c2n1CC(F)(F)F]

262 mg (0.446 mmol) of the compound from Example 5A in 4 ml of phosphoryl chloride were heated at 85° C. for 2 hours. The reaction was then poured into warm water and stirred for 1 hour. A solid formed, which was filtered off and washed with a little water. After drying under high vacuum, this gave 198 mg of the title compound (89% of theory).

LC-MS (Method 1): $R_t$=1.29 min; MS (EIpos): m/z=496 [M+H]$^+$.

$^1$H NMR (400 MHz; DMSO-$d_6$): δ [ppm]=4.86 (q, 2H), 5.86 (s, 2H), 7.15-7.19 (m, 1H), 7.21-7.30 (m, 2H), 7.35-7.41 (m, 1H), 8.49 (dd, 1H), 8.77 (dd, 1H), 12.95 (s, 1H).

Example 7A 2-(2-Fluorophenyl)-N-[(6-oxo-1,4,5,6-tetrahydropyridazin-3-yl)methyl]acetamide

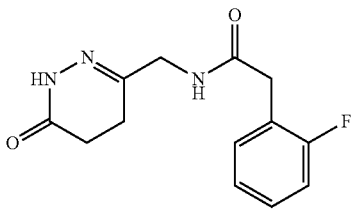 [SMILES: O=C(Cc1ccccc1F)NCC1=NNC(=O)CC1]

200.00 g (1.101 mol) of methyl 5-amino-4-oxopentanoate hydrochloride were initially charged in ethanol (3500 ml), 64.28 ml (1.321 mol) of hydrazine hydrate were added and the mixture was then heated at reflux for 45 min. After cooling, triethylamine (152 ml) was added and the mixture was evaporated to dryness. Water (500 ml) was added to the residue, and the mixture was concentrated. Ethanol (500 ml) was then added, the mixture was concentrated, and then toluene (500 ml) was added twice, followed in each case by evaporation to dryness. The residue (140 g) was dissolved in acetonitrile (500 ml) and, at 0° C., slowly added to a solution of 307.85 g (1.784 mol) of (2-fluorophenyl)acetyl chloride (preparation: Journal of Organic Chemistry; 22; 1957; 879) and 304.86 ml (2.202 mol) of triethylamine in acetonitrile (1500 ml) and molecular sieve. The mixture was stirred at 20° C. for 3 days. The mixture was then filtered and the precipitate was washed with tert-butyl methyl ether and then dried. This gave 458 g of the target compound (90% of theory).

LC-MS (Method 1): $R_t$=0.57 min; MS (EIpos): m/z=264 [M+H]$^+$.

Example 8A 2-(2-Fluorophenyl)-N-[(6-oxo-1,6-dihydropyridazin-3-yl)methyl]acetamide

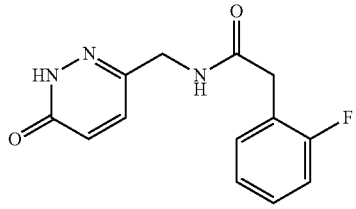 [SMILES: O=C(Cc1ccccc1F)NCc1ccc(=O)[nH]n1]

458 g (1.740 mol) of the compound obtained in Example 7A were initially charged in acetic acid (2250 ml), and the mixture was warmed to 50° C. At this temperature, 98.16 ml (1.914 mol) of bromine were added dropwise with vigorous stirring, and stirring was then continued at 50° C. for 3 h. After cooling, the reaction mixture was concentrated to dryness. The residue was stirred with saturated aqueous sodium bicarbonate solution (4800 ml). The mixture was then filtered and the precipitate was washed with a little water. The filtrate was extracted twice with ethyl acetate. The organic phases were combined, dried and concentrated. This gave 117 g of the target compound (25% of theory).

LC-MS (Method 1): $R_t$=0.56 min; MS (EIpos): m/z=262 [M+H]$^+$.

$^1$H NMR (400 MHz; DMSO-d$_6$): δ [ppm]=3.54 (s, 2H), 4.16 (d, 2H), 6.86 (d, 1H), 7.12-7.16 (m, 2H), 7.27-7.35 (m, 3H), 8.62 (t, 1H), 12.88 (s, 1H).

Example 9A

2-Chloro-7-(2-fluorobenzyl)imidazo[1,5-b]pyridazine

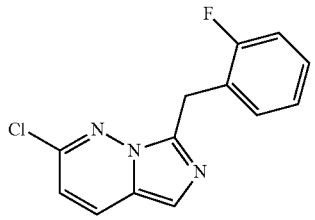 [SMILES: Fc1ccccc1Cc1ncc2ccc(Cl)nn12]

65.00 g (248.79 mmol) of the compound obtained in Example 8A were initially charged in sulpholane (780 ml), 185.52 ml (1.990 mol) of phosphorus oxychloride were added and the mixture was heated to 100° C. for 3 h. Excess phosphorus oxychloride was then distilled off under high vacuum, and the residue was taken up in ethyl acetate and added to a saturated aqueous sodium bicarbonate solution. The mixture was diluted with water and then extracted with ethyl acetate. The organic phases were combined, washed with water, dried over sodium sulphate and concentrated. The residue was purified by chromatography on silica gel (mobile phase: dichloromethane/methanol 20:1→5:1 (v/v)), then washed with water and purified by chromatography on silica gel (mobile phase: dichloromethane/methanol 100:1 v/v). This gave 23.6 g of the target compound (36% of theory).

LC-MS (Method 1): $R_t$=1.00 min; MS (EIpos): m/z=262 [M+H]$^+$.

$^1$H NMR (400 MHz; DMSO-d$_6$): δ [ppm]=4.40 (s, 2H), 6.84 (d, 1H), 7.10-7.33 (m, 4H), 7.55 (s, 1H), 8.19 (d, 1H).

Example 10A 7-(2-Fluorobenzyl)imidazo[1,5-b]pyridazine

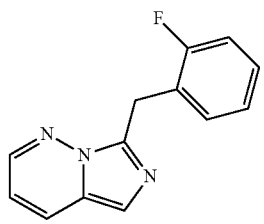 [SMILES: Fc1ccccc1Cc1ncc2cccnn12]

2.004 g of palladium on carbon (5%) were initially charged under argon, and 20.04 g (76.58 mmol) of the compound obtained in Example 9A in ethyl acetate (750 ml) were then added. 21.348 ml (153.159 mmol) of triethylamine were then added, and the reaction mixture was hydrogenated at standard hydrogen pressure and 20° C. for 16 hours. The same amount of catalyst as indicated above was then added, and the reaction mixture was hydrogenated at standard hydrogen pressure and 20° C. for another night. The mixture was then filtered through Celite, the filter cake was washed with ethanol and the filtrate was concentrated and dried under high vacuum. This gave 22.79 g of the target compound (about 100% of theory, contaminated with triethylamine).

LC-MS (Method 1): $R_t$=0.77 min; MS (EIpos): m/z=228 [M+H]$^+$.

$^1$H NMR (400 MHz; DMSO-d$_6$): δ [ppm]=4.44 (s, 2H), 6.70 (dd, 1H), 7.08-7.31 (m, 4H), 7.45 (s, 1H), 8.09 (dd, 1H), 8.28 (dd, 1H).

Example 11A

5-Bromo-7-(2-fluorobenzyl)imidazo[1,5-b]pyridazine

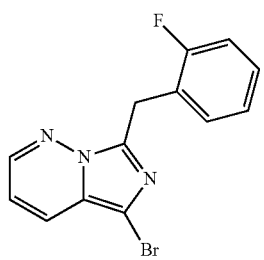

22.46 g (98.837 mmol) of the compound obtained in Example 10A were initially charged in dichloromethane (400 ml), and 17.591 g (98.837 mmol) of N-bromosuccinimide were added. The mixture was then stirred at 20° C. for 10 min. Water was then added to the reaction mixture, the phases were separated and the organic phase was washed with water. The aqueous phase was extracted twice with dichloromethane and the combined organic phases were washed with saturated aqueous sodium chloride solution, dried over sodium sulphate, filtered and concentrated. This gave 22.78 g of the target compound (75% of theory).

LC-MS (Method 1): $R_t$=1.05 min; MS (EIpos): m/z=306, 308 [M+H, bromine pattern]$^+$.

$^1$H NMR (400 MHz; DMSO-$d_6$): δ [ppm]=4.45 (s, 2H), 6.81 (dd, 1H), 7.12-7.34 (m, 4H), 7.94 (dd, 1H), 8.28 (dd, 1H).

Example 12A 7-(2-Fluorobenzyl)imidazo[1,5-b]pyridazine-5-carbonitrile

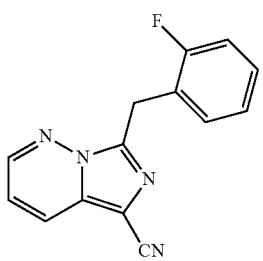 [SMILES: N#Cc1nc(Cc2ccccc2F)n2ncccc12]

1.00 g (3.266 mmol) of the compound obtained in Example 11A were initially charged in dry DMSO (25 ml), 1.170 g (13.066 mmol) of copper(I) cyanide were added and, with stirring, the mixture was heated at 170° C. for 3.5 h. The mixture was filtered through Celite, and the filter cake was washed with ethyl acetate and tetrahydrofuran. The filtrate was then extracted four times with a mixture of saturated aqueous ammonium chloride solution/aqueous ammonia (33%) (3:1, v/v) and washed once with saturated aqueous sodium chloride solution. The phases were separated and the organic phase was dried with sodium sulphate, filtered and concentrated. The residue was treated with ethanol in an ultrasonic bath, and water was then added. The precipitate formed was filtered off, washed with ethanol and then dried under high vacuum. This gave 586 mg of the target compound (71% of theory).

LC-MS (Method 1): $R_t$=0.95 min; MS (EIpos): m/z=253 [M+H]$^+$.

$^1$H NMR (400 MHz; DMSO-$d_6$): δ [ppm]=4.49 (s, 2H), 7.13-7.35 (m, 5H), 8.40 (d, 1H), 8.61 (d, 1H).

Example 13A

5-Fluoro-3-iodo-1-(3,3,4,4,4-pentafluorobutyl)-1H-pyrazolo[3,4-b]pyridine

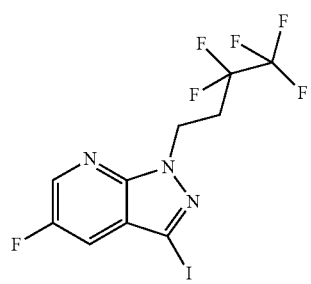 [SMILES: Fc1cnc2c(c1)c(I)nn2CCC(F)(F)C(F)(F)F]

5.0 g (19.010 mmol) of 5-fluoro-3-iodo-1H-pyrazolo[3,4-b]pyridine were initially charged in DMF (100 ml), and then 20.83 g (76.042 mmol) of 1,1,1,2,2-pentafluoro-4-iodobutane, and also 14.86 g (45.65 mmol) of caesium carbonate and 0.63 g (3.802 mmol) of potassium iodide were added. The mixture was stirred at 140° C. overnight. The mixture was then cooled and combined with a prior experiment which had been carried out analogously using 200 mg of 5-fluoro-3-iodo-1H-pyrazolo[3,4-b]pyridine. Solids were filtered off with suction and washed with DMF, and then the filtrate was concentrated under high vacuum. The residue was purified by preparative HPLC (methanol:water gradient). This gave 4.34 g (52% of theory) of the title compound.

LC-MS (Method 2): $R_t$=1.30 min

MS (ESIpos): m/z=410 (M+H)$^+$ $^1$H NMR (400 MHz; DMSO-$d_6$): δ=2.84-3.00 (m, 2H), 4.79 (t, 2H), 7.93 (dd, 1H), 8.71 (dd, 1H).

Example 14A

5-Fluoro-1-(3,3,4,4,4-pentafluorobutyl)-1H-pyrazolo[3,4-b]pyridine-3-carbonitrile

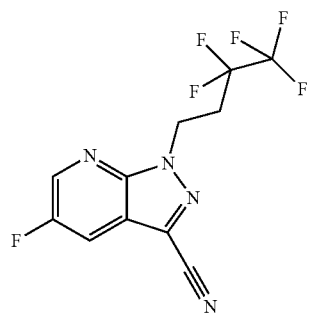 [SMILES: N#Cc1nn(CCC(F)(F)C(F)(F)F)c2ncc(F)cc12]

A suspension of 4.34 g (10.609 mmol) of Example 13A and 1.045 g (11.670 mmol) of copper(I) cyanide was initially charged in DMSO (30 ml) and stirred at 150° C. for 2 h. After cooling, the mixture was filtered through Celite, the filter cake was washed with ethyl acetate and THF and the filtrate was then extracted four times with a solution of saturated aqueous ammonium chloride solution and conc. aqueous ammonia (3:1 v/v). The combined organic phases were washed with saturated aqueous sodium chloride solution, dried over sodium sulphate, filtered and concentrated under reduced pressure.

Yield: 3.19 g (97% of theory)
$^1$H NMR (400 MHz; DMSO-$d_6$): δ=2.94-3.09 (m, 2H), 4.93 (t, 2H), 8.54 (dd, 1H), 8.88 (dd, 1H).

WORKING EXAMPLES

Example 1

6-{5-Fluoro-1-[(3-fluoropyridin-2-yl)methyl]-1H-pyrazolo[3,4-b]pyridin-3-yl}-3-methyl-1H-pyrazolo[3,4-d]pyrimidine-4-amine

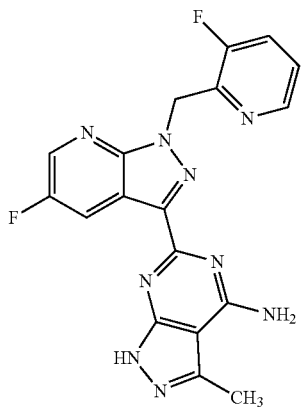 [SMILES: Cc1n[nH]c2nc(-c3nn(Cc4ncccc4F)c4ncc(F)cc34)nc(N)c12]

According to General Procedure 1, 100 mg (0.369 mmol) of Example 2A were reacted with 5-amino-3-methyl-1H-pyrazole-4-carbonitrile.
Yield: 14 mg (10% of theory)
LC-MS (Method 1): R$_t$=0.71 min; MS (EIpos): m/z=394 [M+H]$^+$.
$^1$H NMR (400 MHz; DMSO-$d_6$): δ [ppm]=methyl group, 3H probably under DMSO signal, 5.96 (s, 2H), 7.42-7.46 (m, 1H), 7.76 (t, 1H), 8.28 (d, 1H), 8.67 (s br, 1H), 8.90 (dd, 1H), 12.97 (s br, 1H).

Example 2

N$^3$,N$^3$-Diethyl-6-{5-fluoro-1-[(3-fluoropyridin-2-yl)methyl]-1H-pyrazolo[3,4-b]pyridin-3-yl}-1H-pyrazolo[3,4-d]pyrimidine-3,4-diamine

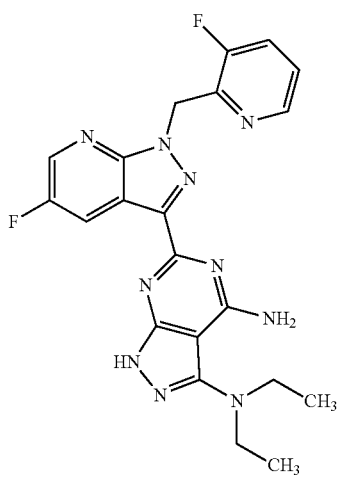 [SMILES: CCN(CC)c1n[nH]c2nc(-c3nn(Cc4ncccc4F)c4ncc(F)cc34)nc(N)c12]

According to General Procedure 1, 100 mg (0.369 mmol) of Example 2A were reacted with 5-amino-3-(diethylamino)-1H-pyrazole-4-carbonitrile.

Yield: 37 mg (22% of theory)
LC-MS (Method 1): R$_t$=0.93 min; MS (EIpos): m/z=451 [M+H]$^+$.
$^1$H NMR (400 MHz; DMSO-$d_6$): δ [ppm]=1.04 (t, 6H), 3.22 (q, 4H), 5.96 (s, 2H), 7.42-7.46 (m, 1H), 7.75-7.80 (m, 1H), 8.27-8.29 (m, 1H), 8.66 (dd, 1H), 8.90 (dd, 1H), 12.55 (s br, 1H).

Example 3

2-{5-Fluoro-1-[(3-fluoropyridin-2-yl)methyl]-1H-pyrazolo[3,4-b]pyridin-3-yl}pyrido[2,3-d]pyrimidine-4-amine

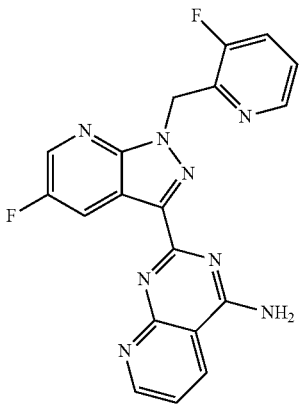 [SMILES: Nc1nc(-c2nn(Cc3ncccc3F)c3ncc(F)cc23)nc2ncccc12]

According to General Procedure 1, 100 mg (0.369 mmol) of Example 2A were reacted with 2-aminopyridinecarbonitrile.
Yield: 19 mg (13% of theory)
LC-MS (Method 1): R$_t$=0.71 min; MS (EIpos): m/z=391 [M+H]$^+$.
$^1$H NMR (400 MHz; DMSO-$d_6$): δ [ppm]=6.01 (s, 2H), 7.43-7.47 (m, 1H), 7.52 (dd, 1H), (7.76-7.81 (m, 1H), 8.28-8.30 (m, 1H), 8.33 (s br, 2H), 8.67-8.70 (m, 2H), 8.90 (dd, 1H), 9.01 (dd, 1H).

Example 4

6-{5-Fluoro-1-[(3-fluoropyridin-2-yl)methyl]-1H-pyrazolo[3,4-b]pyridin-3-yl}-3-methoxy-1H-pyrazolo[3,4-d]pyrimidine-4-amine

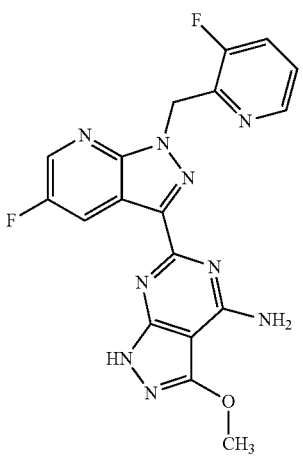 [SMILES: COc1n[nH]c2nc(-c3nn(Cc4ncccc4F)c4ncc(F)cc34)nc(N)c12]

According to General Procedure 1, 100 mg (0.369 mmol) of Example 2A were reacted with 5-amino-3-methoxy-1H-pyrazole-4-carbonitrile.

Yield: 18 mg (12% of theory)

LC-MS (Method 1): $R_t$=0.79 min; MS (EIpos): m/z=410 [M+H]$^+$.

$^1$H NMR (400 MHz; DMSO-d$_6$): δ [ppm]=3.98 (s, 3H), 5.96 (s, 2H), 7.42-7.46 (m, 1H), 7.75-7.80 (m, 1H), 8.27-8.29 (m, 1H), 8.66 (dd, 1H), 8.88 (dd, 1H), 12.41 (s br, 1H).

Example 5

6-[(Cyclopropylmethyl)amino]-2-[5-fluoro-1-(2-fluorobenzyl)-1H-pyrazolo[3,4-b]pyridin-3-yl]-7-(2,2,2-trifluoroethyl)-7,9-dihydro-8H-purin-8-one

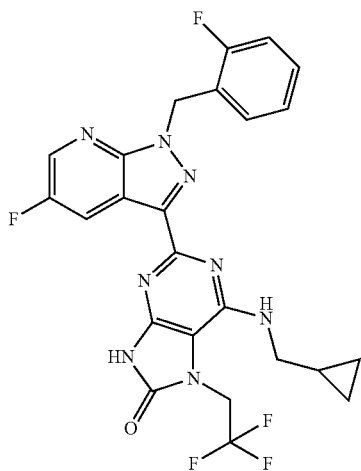 [SMILES: O=c1[nH]c2nc(-c3nn(Cc4ccccc4F)c4ncc(F)cc34)nc(NCC3CC3)c2n1CC(F)(F)F]

In a microwave vessel with stirrer magnet, 90 mg (0.182 mmol) of Example 6A were dissolved in 2 ml of NMP, aminomethylcyclopropane (0.5 ml) was added and the mixture was then heated at 150° C. under microwave irradiation for 3 h. The reaction mixture was purified by preparative HPLC (mobile phase: acetonitrile/water with 0.05% of formic acid, gradient).

Yield: 18 mg (18% of theory)

LC-MS (Method 1): $R_t$=1.26 min; MS (EIpos): m/z=531 [M+H]$^+$.

$^1$H NMR (400 MHz; DMSO-d$_6$): δ [ppm]=0.32-0.35 (m, 2H), 0.43-0.48 (m, 2H), 1.23-1.28 (m, 1H), 3.51 (dd, 2H), 4.96 (q, 2H), 5.82 (s, 2H), 6.91 (t, 1H), 7.13-7.17 (m, 1H), 7.20-7.27 (m, 2H), 7.35-7.40 (m, 1H), 8.57 (dd, 1H), 8.72 (dd, 1H), 11.99 (s, 1H).

Example 6

2-[5-Fluoro-1-(2-fluorobenzyl)-1H-pyrazolo[3,4-b]pyridin-3-yl]-7-(2,2,2-trifluoroethyl)-6-[(3,3,3-trifluoropropyl)amino]-7,9-dihydro-8H-purin-8-one

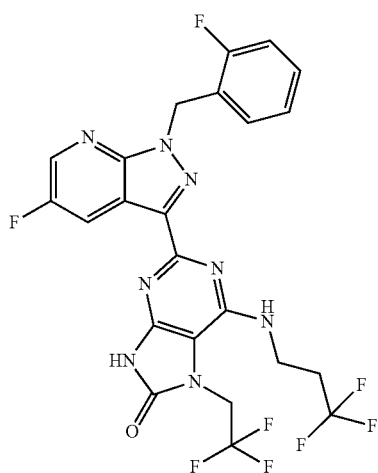 [SMILES: O=c1[nH]c2nc(-c3nn(Cc4ccccc4F)c4ncc(F)cc34)nc(NCCC(F)(F)F)c2n1CC(F)(F)F]

In a microwave vessel with stirrer magnet, 90 mg (0.182 mmol) of Example 6A were dissolved in 2 ml of NMP, 122 mg (0.817 mmol) of 3,3,3-trifluoropropyl-1-amine hydrochloride and 0.164 ml (0.944 mmol) of N,N-diisopropylethylamine were added and the mixture was then heated at 150° C. under microwave irradiation for 3 h. The reaction mixture was purified by preparative HPLC (mobile phase: acetonitrile/water with 0.05% of formic acid, gradient). 54 mg still containing starting material were isolated. In a microwave vessel with stirrer magnet, 44 mg of this mixture were then dissolved in 1 ml of NMP, 60 mg (0.405 mmol) of 3,3,3-trifluoropropyl-1-amine hydrochloride and 81 μl (0.468 mmol) of N,N-diisopropylethylamine were added and the mixture was then heated at 150° C. under microwave irradiation for 6 h. The reaction mixture was purified by preparative HPLC (mobile phase: acetonitrile/water with 0.05% of formic acid, gradient).

Yield: 34 mg (33% of theory)

LC-MS (Method 1): $R_t$=1.22 min; MS (EIpos): m/z=573 [M+H]$^+$.

$^1$H NMR (400 MHz; DMSO-d$_6$): δ [ppm]=2.65-2.72 (m, 2H), 3.85-3.90 (q, 2H), 4.90-4.97 (q, 2H), 5.82 (s, 2H), 6.97 (t, 1H), 7.16 (t, 1H), 7.20-7.29 (m, 2H), 7.34-7.40 (m, 1H), 8.46 (dd, 1H), 8.72 (dd, 1H), 12.09 (s, 1H).

Example 7

6-[7-(2-Fluorobenzyl)imidazo[1,5-b]pyridazin-5-yl]-3-methyl-1H-pyrazolo[3,4-d]pyrimidine-4-amine

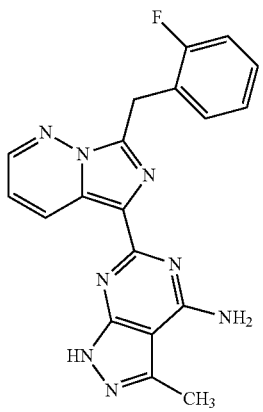 [SMILES: Cc1n[nH]c2nc(-c3nc(Cc4ccccc4F)n4ncccc34)nc(N)c12]

According to General Procedure 1, 100 mg (0.369 mmol) of Example 12A were reacted with 5-amino-3-methyl-1H-pyrazole-4-carbonitrile at 200° C.

Yield: 19 mg (13% of theory)

LC-MS (Method 1): $R_t$=0.77 min; MS (EIpos): m/z=375 [M+H]$^+$.

$^1$H NMR (400 MHz; DMSO-d$_6$): δ [ppm]=methyl group, 3H probably under DMSO signal, 4.50 (s, 2H), 6.95 (dd, 1H), 7.12-7.23 (m, 2H), 7.29-7.34 (m, 2H), 8.41 (dd, 1H), 9.11 (dd, 1H), 12.80 (s br, 1H).

Example 8

6-[5-Fluoro-1-(3,3,4,4,4-pentafluorobutyl)-1H-pyrazolo[3,4-b]pyridin-3-yl]-3-methyl-1H-pyrazolo[3,4-d]pyrimidine-4-amine

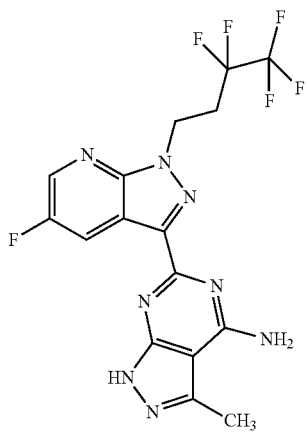 [SMILES: Cc1n[nH]c2nc(-c3nn(CCC(F)(F)C(F)(F)F)c4ncc(F)cc34)nc(N)c12]

According to General Procedure 2, 200 mg (0.65 mmol) of Example 14A, 5-fluoro-1-(3,3,4,4,4-pentafluorobutyl)-1H-pyrazolo[3,4-b]pyridine-3-carbonitrile, were reacted with 5-amino-3-methyl-1H-pyrazole-4-carbonitrile.

Yield: 6.6 mg (2% of theory)

LC-MS (Method 1): $R_t$=0.92 min; MS (EIpos): m/z=431 [M+H]$^+$.

$^1$H NMR (400 MHz; DMSO-d$_6$): δ [ppm]=2.57 (s, 3H), 2.90-3.12 (m, 2H), 4.88 (t, 2H), 7.50 (br. s, 2H), 8.68-8.74 (m, 1H), 8.94 (dd, 1H), 13.03 (br. s, 1H).

Example 9

N3,N3-Diethyl-6-{5-fluoro-1-[(3-fluoropyridin-2-yl)methyl]-1H-pyrazolo[3,4-b]pyridin-3-yl}-1H-pyrazolo[3,4-d]pyrimidine-3,4-diamine

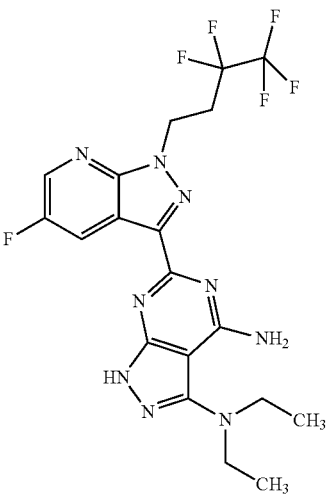 [SMILES: CCN(CC)c1n[nH]c2nc(-c3nn(CCC(F)(F)C(F)(F)F)c4ncc(F)cc34)nc(N)c12]

According to General Procedure 2, 100 mg (0.32 mmol) of Example 14A, 5-fluoro-1-(3,3,4,4,4-pentafluorobutyl)-1H-pyrazolo[3,4-b]pyridine-3-carbonitrile, were reacted with 5-amino-3-(diethylamino)-1H-pyrazole-4-carbonitrile. The mixture was then heated at 200° C. for a further 2 h and finally at 160° C. under microwave irradiation for 10 h.

Yield: 5.2 mg (3% of theory)

LC-MS (Method 1): $R_t$=1.09 min; MS (EIpos): m/z=488 [M+H]$^+$.

$^1$H NMR (400 MHz; DMSO-d$_6$): δ [ppm]=1.05 (t, 6H), 2.86-3.13 (m, 3H), 3.22 (q, 4H), 4.88 (t, 2H), 7.22 (br. s, 2H), 8.70 (dd, 1H), 8.95 (dd, 1H), 12.61 (s, 1H).

Example 10

2-[5-Fluoro-1-(3,3,4,4,4-pentafluorobutyl)-1H-pyrazolo[3,4-b]pyridin-3-yl]pyrido[2,3-d]pyrimidine-4-amine

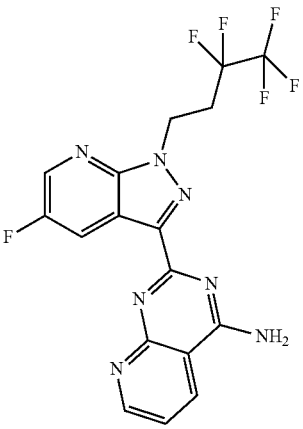 [SMILES: Nc1nc(-c2nn(CCC(F)(F)C(F)(F)F)c3ncc(F)cc23)nc2ncccc12]

According to General Procedure 2, 200 mg (0.65 mmol) of Example 14A, 5-fluoro-1-(3,3,4,4,4-pentafluorobutyl)-1H-pyrazolo[3,4-b]pyridine-3-carbonitrile, were reacted with 2-aminopyridinecarbonitrile. The mixture was then heated at 180° C. under microwave irradiation for a further 3 h. Finally, a further 80 mg (0.67 mmol) of 2-aminopyridinecarbonitrile and 73 mg (0.65 mmol) of potassium tert-butoxide were added, and the mixture was heated at 180° C. under microwave irradiation for 3 h.

Yield: 6.6 mg (2% of theory)

LC-MS (Method 1): $R_t$=0.89 min; MS (EIpos): m/z=428 [M+H]$^+$.

$^1$H NMR (400 MHz, DMSO-$d_6$): δ [ppm]=2.94-3.12 (m, 2H), 4.93 (t, 2H), 7.50-7.59 (m, 1H), 8.37 (br. s., 1H), 8.70 (d, 1H), 8.75 (br. s., 1H), 8.91 (dd, 1H), 9.04 (br. s., 1H).

B. ASSESSMENT OF PHARMACOLOGICAL EFFICACY

The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders. To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% ($IC_{50}$ value). The standard administration volume is 5 µl; the DMSO content in the bath solution corresponds to 0.1%.

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 2):

TABLE 2

| Example | MEC [µm] |
|---------|----------|
| 1 | 0.3 |
| 2 | 0.1 |
| 3 | 10 |
| 4 | 0.3 |
| 5 | 0.3 |
| 7 | 0.01 |
| 8 | 0.1 |

TABLE 2-continued

| Example | MEC [µm] |
|---------|----------|
| 9 | 0.03 |
| 10 | 0.3 |

B-3. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vet-BonD™, 3M). The transmitter housing is fixed intraperitoneally to the abdominal wall muscle, and layered closure of the wound is performed.

An antibiotic (Tardomyocel COMP, Bayer, 1 ml/kg s.c.) is administered postoperatively for prophylaxis of infection.

Substances and Solutions

Unless indicated otherwise, the substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight.

A solvent-treated group of animals is employed as control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
  systolic blood pressure (SBP)
  diastolic blood pressure (DBP)
  mean arterial pressure (MAP)
  heart rate (HR)
  activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9:00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7:00 am on the day of the experiment to 9:00 am on the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed in paper form sorted by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration The pharmacokinetic parameters of the compounds according to the invention are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at −20° C. until further processing.

An internal standard (which may also be a chemically unrelated substance) is added to the samples of the compounds according to the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by means of LC-MS/MS using C18 reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $c_{blood}/c_{plasma}$ value.

B-5. Metabolic Study

To determine the metabolic profile of the compounds according to the invention, they are incubated with recombinant human cytochrome $P^{450}$ (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM NADP+, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analysed directly or stored at −20° C. until analysis.

The analysis is effected by means of high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound according to the invention in the incubation mixtures.

C. WORKING EXAMPLES OF PHARMACEUTICAL COMPOSITIONS

The compounds according to the invention can be converted to pharmaceutical formulations as follows:

Tablet:

Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm

Production:

The mixture of compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.

Suspension which can be Administered Orally:

Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Production:

The Rhodigel is suspended in ethanol and the compound according to the invention is added to the suspension. The water is added while stirring. The mixture is stirred for about 6 h until swelling of the Rhodigel is complete.

Solution which can be Administered Orally:

Composition:

500 mg of the compound according to the invention, 2.5 g of polysorbate and 97 g of polyethylene glycol 400. A single dose of 100 mg of the compound according to the invention corresponds to 20 g of oral solution.

Production:

The compound according to the invention is suspended in the mixture of polyethylene glycol and polysorbate while stirring. The stirring operation is continued until dissolution of the compound according to the invention is complete.

i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:

1. A compound of the formula (I)

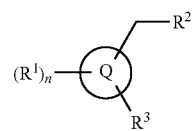

(I)

in which $R^1$ represents $R^{1A}$, $R^{1B}$ or $R^{1C}$, n represents a number 0 or 1, the ring Q represents a group of the formula

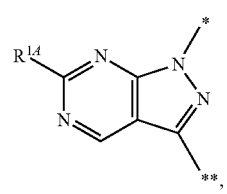

(a-1-1)

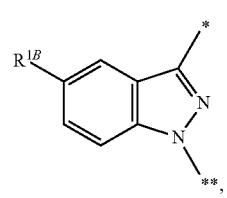

(b-1-1)

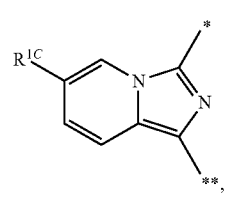

(c-1-1)

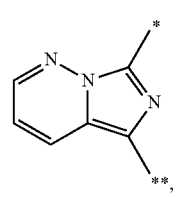

(c-1-2)

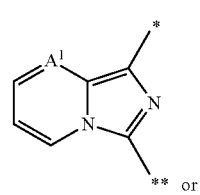

(d-1)

or

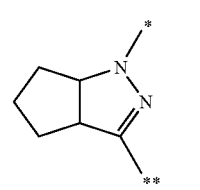

(I-1-1)

where
* represents the point of attachment to —CH$_2$—R$^2$,
** represents the point of attachment to R$^3$,
R$^{1A}$ represents hydrogen or methyl,
R$^{1B}$ represents hydrogen or fluorine,
R$^{1C}$ represents hydrogen or chlorine,
A$^1$ represents N or CH,
R$^2$ represents 3,3,3-trifluoroprop-1-yl, 2,2,3,3-tetrafluoroprop-1-yl, 2,2,3,3,3-pentafluoroprop-1-yl, phenyl or pyridyl,
  where phenyl is substituted by 1 to 3 fluorine substituents,
  and
  where pyridyl may be substituted by 1 fluorine substituent,
R$^3$ represents a group of the formula

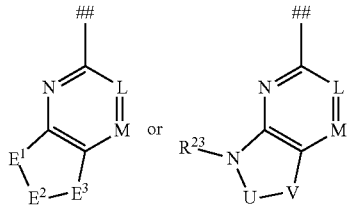

where
## represents the point of attachment to the ring Q,
L represents N,
M represents CR$^4$,
  in which
    R$^4$ represents —R$^5$, OR$^6$ or NR$^7$R$^8$,
      in which
        R$^5$ represents hydrogen or (C$_1$-C$_4$)-alkyl,
          in which (C$_1$-C$_4$)-alkyl for its part may be substituted by 1 or 2 substituents independently of one another selected from the group consisting of fluorine, difluoromethyl, trifluoromethyl, cyclopropyl, cyclobutyl, —(C=O)$_p$—OR$^9$ and —C(=O)$_p$—NR$^9$R$^{10}$,
            in which
              p represents the number 0,
              R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
        R$^6$ represents (C$_1$-C$_6$)-alkyl or pyrazolyl,
          in which (C$_1$-C$_6$)-alkyl may be substituted by 1 to 3 substituents independently of one another selected from the group consisting of fluorine, trifluoromethyl, —(C=O)$_p$—OR$^9$ and —C(=O)$_p$—NR$^9$R$^{10}$,
            in which
              p represents the number 0 or 1,
              R$^9$ and R$^{10}$ independently of one another each represent hydrogen or methyl,
              or
              R$^9$ and R$^{10}$ together with the atom(s) to which they are respectively attached form an azetidinyl, pyrrolidinyl, piperidinyl, piperazinyl or morpholinyl ring,
                in which the azetidinyl, pyrrolidinyl, piperidinyl, piperazinyl and morpholinyl ring for its part may be substituted by 1 or 2 substituents independently of one another selected from the group consisting of fluorine, trifluoromethyl, methyl, ethyl, hydroxy, oxo, methoxy, ethoxy, amino, methylamino, ethylamino, dimethylamino and diethylamino,
          and
          in which pyrazolyl may be substituted by 1 or 2 substituents independently of one another selected from the group consisting of fluorine, difluoromethyl, trifluoromethyl, 2,2,2-trifluoroethyl, 1,1,2,2,2-pentafluoroethyl, methyl, cyclopropyl, cyclobutyl and cyclopentyl,
        R$^7$ represents hydrogen, methyl or ethyl,
        R$^8$ represents hydrogen, (C$_1$-C$_6$)-alkyl, oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl or pyrimidinyl,
          in which (C$_1$-C$_6$)-alkyl may be substituted by 1 to 3 substituents independently of one another selected from the group consisting of fluorine, difluoromethyl, trifluoromethyl, cyclopropyl, cyclobutyl, cyclopentyl, trifluoromethoxy, —(C=O)$_p$—OR$^9$, —(C=O)$_p$—NR$^9$R$^{10}$, tetrahydrofuranyl, pyrrolidinyl, tetrahydropyranyl, phenyl, furanyl, pyrazolyl, imidazolyl, triazolyl and pyridyl,
            in which
              p represents the number 0 or 1,
              R$^9$ and R$^{10}$ independently of one another each represent hydrogen, methyl, ethyl, trifluoromethyl, 2,2,2-trifluoroethyl, 1,1,2,2,2-pentafluoroethyl, cyclopropyl or cyclobutyl,
            and
            in which tetrahydrofuranyl, pyrrolidinyl, tetrahydropyranyl, phenyl, furanyl, pyrazolyl, imidazolyl, triazolyl and pyridyl for their part may be substituted by 1 or 2 substituents independently of one another selected from the group consisting of fluorine, chlorine, cyano, difluoromethyl, trifluoromethyl, methyl, ethyl, oxo, difluoromethoxy, trifluoromethoxy, methoxy and ethoxy,
          and
          in which oxetanyl, azetidinyl, tetrahydrofuranyl, pyrrolidinyl, tetrahydropyranyl, piperidinyl, piperazinyl, morpholinyl, phenyl, pyrazolyl, oxazolyl, thiazolyl, triazolyl, oxadiazolyl, thiadiazolyl, pyridyl and pyrimidinyl may be substituted by 1 to 3 substituents independently of one another selected from the group consisting of fluorine, difluoromethyl, trifluoromethyl, methyl, ethyl and trifluoromethoxy,
E$^1$ represents NR$^{18}$,
  in which
    R$^{18}$ represents hydrogen,
E$^2$ represents N,
E$^3$ represents N or CR$^{19}$,
  in which
    R$^{19}$ represents hydrogen, fluorine, difluoromethyl, trifluoromethyl, (C$_1$-C$_4$)-alkyl or a group of the formula -M-R$^{13}$,
      in which (C$_1$-C$_4$)-alkyl may be substituted by 1 to 3 substituents independently of one another selected from the group consisting of fluorine, trifluoromethyl, cyclopropyl and cyclobutyl, and in which M represents a bond, methylene, ethane-1,2-diyl or propane-1,3-diyl, $R^{13}$ represents —(C=O)$_r$—OR$^{14}$, —(C=O)$_r$—NR$^{14}$R$^{15}$, phenyl, thiazolyl, triazolyl, oxadiazolyl, thiadiazolyl or pyrimidinyl, in which r represents the number 0 or 1, $R^{14}$ and $R^{15}$ independently of one another each represent hydrogen, methyl, ethyl, cyclopropyl, cyclobutyl or phenyl, in which methyl and ethyl may additionally be substituted by 1 or 2 substituents independently of one another selected from the group consisting of fluorine, difluoromethyl, trifluoromethyl, cyclopropyl, cyclobutyl, hydroxy, trifluoromethoxy and methoxy, and in which phenyl, thiazolyl, triazolyl, oxadiazolyl, thiadiazolyl and pyrimidinyl may each in turn be substituted by 1 or 2 substituents selected independently from the group consisting of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl, U represents C(=O), V represents NR$^{24}$, in which $R^{24}$ represents trideuteromethyl, (C$_1$-C$_6$)-alkyl, cyclopropyl, cyclobutyl, azetidin-3-yl, pyrrolidin-3-yl or piperidin-4-yl, in which (C$_1$-C$_6$)-alkyl for its part may be substituted by 1 to 3 substituents independently of one another selected from the group consisting of fluorine, trifluoromethyl, cyclopropyl, cyclobutyl, hydroxy, oxetanyl and morpholin-4-yl, and in which azetidin-3-yl, pyrrolidin-3-yl and piperidin-4-yl for their part may be substituted by 1 or 2 substituents independently of one another selected from the group consisting of fluorine, trifluoromethyl, 2,2-difluoroethyl, 2,2,2-trifluoroethyl, cyclopropyl and cyclobutyl, $R^{23}$ represents hydrogen, and salts thereof.

2. A method for the treatment of heart failure, angina pectoris, and hypertension comprising administering an effective amount of the compound of claim 1 to a human or animal in need thereof.

3. A pharmaceutical composition comprising the compound of claim 1 and an inert, non-toxic, pharmaceutically suitable excipient.

4. The pharmaceutical composition of claim 3, comprising a further active compound selected from the group consisting of an organic nitrate, an NO donor, a cGMP-PDE inhibitor, an antithrombotic agent, a hypotensive agent and a lipid metabolism modifier.

5. A method of treatment of heart failure, angina pectoris, and hypertension comprising administering an effective amount of the pharmaceutical composition of claim 3 to a human or animal in need thereof.

6. A method of treatment of heart failure, angina pectoris, and hypertension comprising administering an effective amount of the pharmaceutical composition of claim 4 to a human or animal in need thereof.

* * * * *